(12) United States Patent
Medoff et al.

(10) Patent No.: US 9,683,250 B2
(45) Date of Patent: *Jun. 20, 2017

(54) PROCESSING PAPER FEEDSTOCKS

(71) Applicant: XYLECO, INC., Woburn, MA (US)

(72) Inventors: Marshall Medoff, Brookline, MA (US); Thomas Craig Masterman, Rockport, MA (US)

(73) Assignee: XYLECO, INC., Wakefield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/745,208

(22) Filed: Jun. 19, 2015

(65) Prior Publication Data

US 2015/0284757 A1 Oct. 8, 2015

Related U.S. Application Data

(63) Continuation of application No. 13/396,365, filed on Feb. 14, 2012, now abandoned.

(60) Provisional application No. 61/442,710, filed on Feb. 14, 2011.

(51) Int. Cl.
| | |
|---|---|
| C12P 19/14 | (2006.01) |
| C12P 19/02 | (2006.01) |
| C12P 7/14 | (2006.01) |
| C12M 1/00 | (2006.01) |
| C12M 1/40 | (2006.01) |
| C12M 1/02 | (2006.01) |
| C12P 7/10 | (2006.01) |
| C13K 1/02 | (2006.01) |
| C13K 13/00 | (2006.01) |

(52) U.S. Cl.
CPC ............ *C12P 19/14* (2013.01); *C12M 21/18* (2013.01); *C12M 27/00* (2013.01); *C12M 29/06* (2013.01); *C12P 7/10* (2013.01); *C12P 7/14* (2013.01); *C12P 19/02* (2013.01); *C13K 1/02* (2013.01); *C13K 13/002* (2013.01); *C12P 2201/00* (2013.01); *C12P 2203/00* (2013.01); *Y02E 50/16* (2013.01)

(58) Field of Classification Search
None
See application file for complete search history.

(56) References Cited

U.S. PATENT DOCUMENTS

| | | |
|---|---|---|
| 3,334,868 A | 8/1967 | Lage |
| 3,990,944 A | 11/1976 | Gauss |
| 4,038,122 A * | 7/1977 | DeLigt .................... B31F 1/28 156/205 |
| 4,176,522 A | 12/1979 | Holtzapple et al. |
| 4,242,455 A | 12/1980 | Muller |
| 4,243,750 A | 1/1981 | Muller et al. |
| 4,266,027 A | 5/1981 | Muller |
| 4,304,649 A | 12/1981 | Han |
| 4,426,450 A | 1/1984 | Donofrio |
| 5,779,996 A | 7/1998 | Stormo |
| 5,876,505 A | 3/1999 | Klyosov et al. |
| 6,455,306 B1 | 9/2002 | Goldstein et al. |
| 2003/0211130 A1 | 11/2003 | Sanders et al. |
| 2004/0050764 A1 | 3/2004 | Perriello |
| 2004/0053373 A1 | 3/2004 | Foody et al. |
| 2005/0058822 A1* | 3/2005 | Ittel ........................ B32B 27/12 428/304.4 |
| 2007/0037259 A1 | 2/2007 | Hennessey et al. |
| 2007/0134781 A1 | 6/2007 | Agblevor |
| 2007/0148750 A1 | 6/2007 | Hoshino et al. |
| 2007/0172945 A1 | 7/2007 | O'Kennedy et al. |
| 2007/0200262 A1 | 8/2007 | Hills |
| 2008/0139865 A1 | 6/2008 | Galliher et al. |
| 2008/0193991 A1 | 8/2008 | Allen et al. |
| 2008/0202504 A1 | 8/2008 | Hilst |
| 2009/0181433 A1 | 7/2009 | Chotani et al. |
| 2010/0297705 A1 | 11/2010 | Medoff et al. |

FOREIGN PATENT DOCUMENTS

| | | |
|---|---|---|
| BE | 414030 | 3/1936 |
| CN | 2142464 | 9/1993 |
| CN | 2334762 | 8/1999 |
| CN | 2762897 | 3/2006 |
| CN | 1844347 | 10/2006 |
| DE | 2310256 | 9/1973 |
| GB | 470898 | 8/1937 |
| JP | 1017701 | 1/1989 |
| JP | 2005229822 | 9/2005 |
| JP | 2006121954 | 5/2006 |
| JP | 2008121954 | 5/2006 |
| JP | 2008161137 | 7/2008 |
| JP | 2009045037 | 3/2009 |
| JP | 2010041923 | 2/2010 |

(Continued)

OTHER PUBLICATIONS

Hitoshi (JP 2006121954) (EPO translation).*
Kalaichelvi et al. "Mixing time estimation and analysis in a jet mixer", ARPN Journal of Engineering and Applied Sciences 2(5): 35-43, 2007.*
Bergeron et al. "Wastepaper as a feedstock for ethanol production" No. NREL/TP-232-4237. National Renewable Energy Lab., Golden, CO (United States), 1991.*
Woodward "Milk Carton", from How Products are Made webpage, http://www.madehow.com/Volume-4/Milk-Carton.html, copyright 2017.*

(Continued)

*Primary Examiner* — Emily Cordas
(74) *Attorney, Agent, or Firm* — Leber IP Law

(57) ABSTRACT

Methods of processing paper feedstocks are provided, as well as intermediates and products made using such methods. Certain types of paper feedstocks, in particular highly pigmented papers, and/or highly loaded papers such as paper that has been color printed, e.g., magazines, and high basis weight coated papers, e.g., magazine stock, are utilized to produce useful intermediates and products, such as energy, fuels, foods or materials.

29 Claims, 26 Drawing Sheets

(56) References Cited

FOREIGN PATENT DOCUMENTS

| | | | |
|---|---|---|---|
| JP | 2010153328 | 7/2010 | |
| JP | 2011024545 | 2/2011 | |
| JP | 2012010684 | 1/2012 | |
| WO | 2005078140 | 8/2005 | |
| WO | 2005108549 | 11/2005 | |
| WO | 2006056838 | 6/2006 | |
| WO | 2006110901 | 10/2006 | |
| WO | 2006110902 | 10/2006 | |
| WO | 2008144878 | 12/2008 | |
| WO | WO 2009134791 A2 * | 11/2009 | ............. A23K 1/007 |

OTHER PUBLICATIONS

Goyal, "Paper Basis Weight", Pulp and Paper Resources and Information Site, available online, Oct. 2007.
Merck, "Potato Dextrose Broth Manual", Cat. No. 1.00510.0500, available online, 2002.
Kang, Li et al., "Bioconversion of Kraft Paper Mill Sludges to Ethanol by SSF and SSCF," published online: Jan. 23, 2010, Received May 19, 2009, Accepted: Dec. 16, 2009, Department of Chemical Engineering, Auburn University, Auburn, AL 368.
Wayman, Morris et al., "Bioconversion of Waste Paper to Ethanol," Department of Chemical Engineering and Applied Chemistry, University of Toronto, Toronto, Canada M5S 1A4, Received Nov. 14, 1991; accepted Dec. 12, 1991, Process Biochemistry 27 (1992), Elsevier Science Publishers Ltd. England, pp. 239-245.
Database Compendex (Online) Engineering Information, Inc., New York, NY, US, Jun. 2000 (Jun. 2000), Yamanda N. et al., "Decomposition Behavior of Waste Paper With Hot Compressed Water," XP002679607, Database accession No. E2000445334468 abstract & Nihon Enerugi Gakkaishi/Journal of the Japan Institute of Energy 2000 Jun Maruzen Co. Ltd., vol. 79, No. 6, Jun. 2000 (Jun. 2000), pp. 540-547.
International Search Report for corresponding application PCT/US2012/024970, mailed Jul. 20, 2012, 7 pages.
Wilson, "Filler and Coating Pigments for Papermakers", Industrial Minerals and Rocks: Commodities, Markets, and Uses (7th Edition), Edited by Kogel et al., Part III (96): 1287-3000, 2006.
Walas, "Mixing and Agitation", Chapter 10, Chemical Process Equipment Selection and Design, 1990, pp. 287-304.
Onishi et al., "Feasibility Study on Using a Single Mixer Pump for Tank 241-AN-101 Waste Retrieval" PNNL-14105, 54 pgs. Jan. 2003.
ISR and Written Opinion for PCT/US2010/035315, EPO as ISA, mailed Feb. 4, 2011, 18 pages.
Myers et al., "Optimize Mixing by Using the Proper Baffles" CEP Feb. 2002, pp. 42-47.
Olofsson et al. "A short review on SSF—an interesting process option for ethanol production from lignocellulosic feedstocks", Biotechnology for Biofuels, 2008, 1:7, 14 pages.
Pulp Bleaching Technology, Chapter 4 from "Technologies for Reducing Dioxin in the Manufacture of Bleached Wood Pulp", OTA-BP-O-54 (Washington, DC: U.S. Government Printing Office, May 1989), 14 pages.
Office Action—U.S. Appl. No. 14/745,123, dated Feb. 11, 2016, 18 pages.
Dasari, "High_Solids Saccharification and Viscosity Studies in a Scraped Surface Bio-Reactor", B.Tech., Osmania University, India, 2004, Department of Chemical Engineering, University of Louisville, Lousville, KY, May 2008, 270 pages.
Reese, "Inactivation of Cellulase by Shaking and its Prevention by Surfactants", Journal of Applied Biochemistry, vol. 2, 1980, pp. 36-39.
Search Report—Corresponding Chinese Application No. 2012800057564, dated Mar. 7, 2016, 2 pages.
Search Report—Corresponding Chinese Application No. 2012800057564, dated Mar. 28, 2016, 2 pages.

* cited by examiner

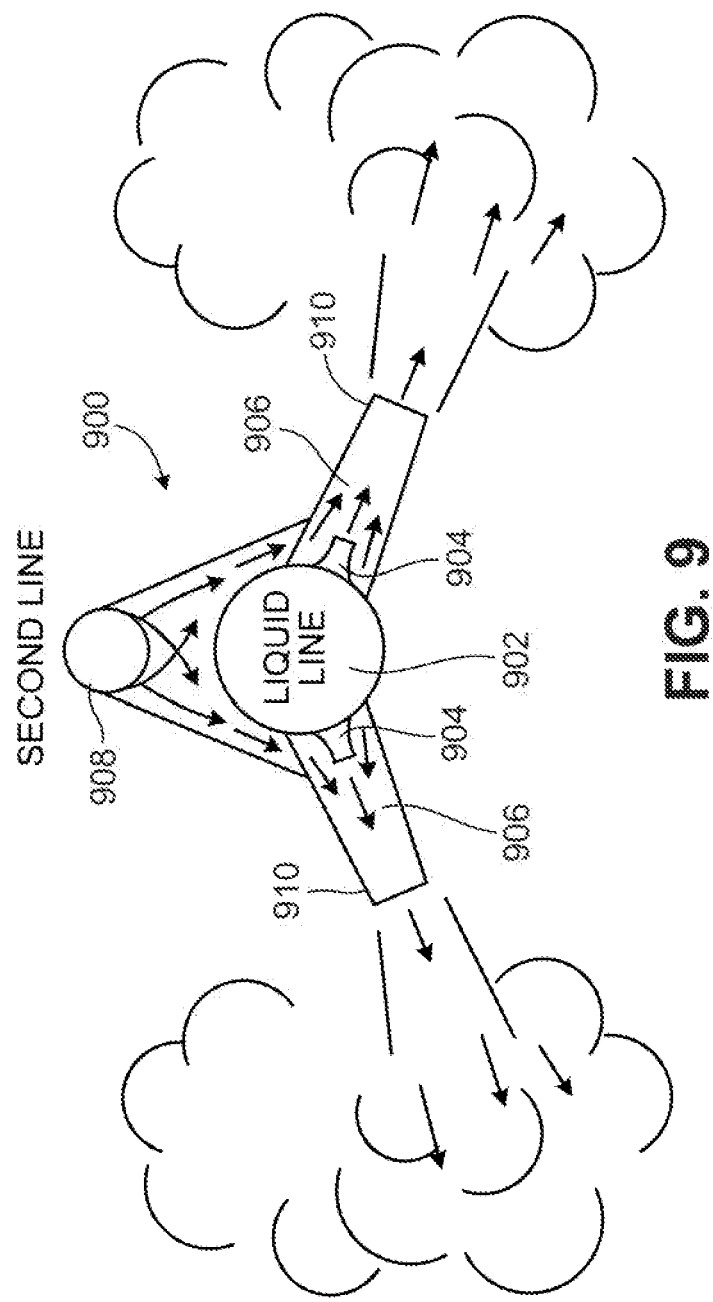

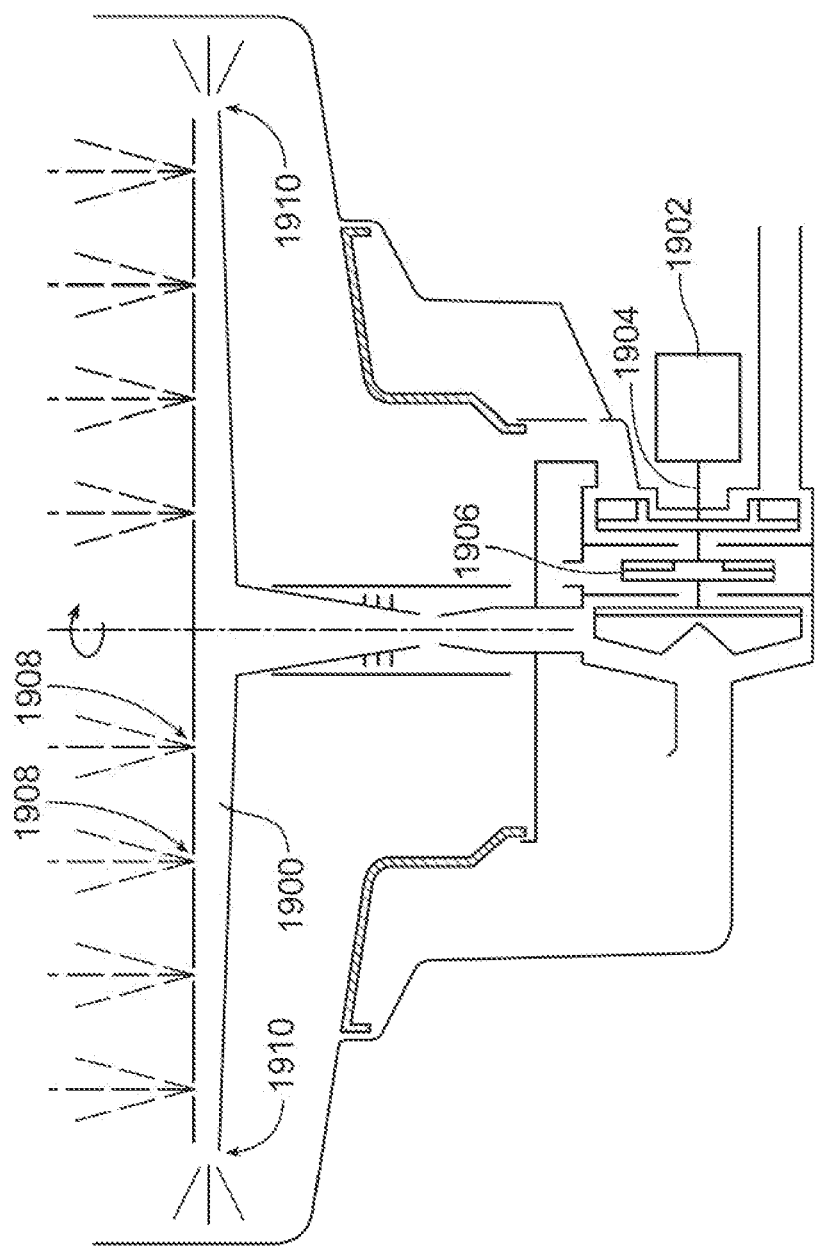

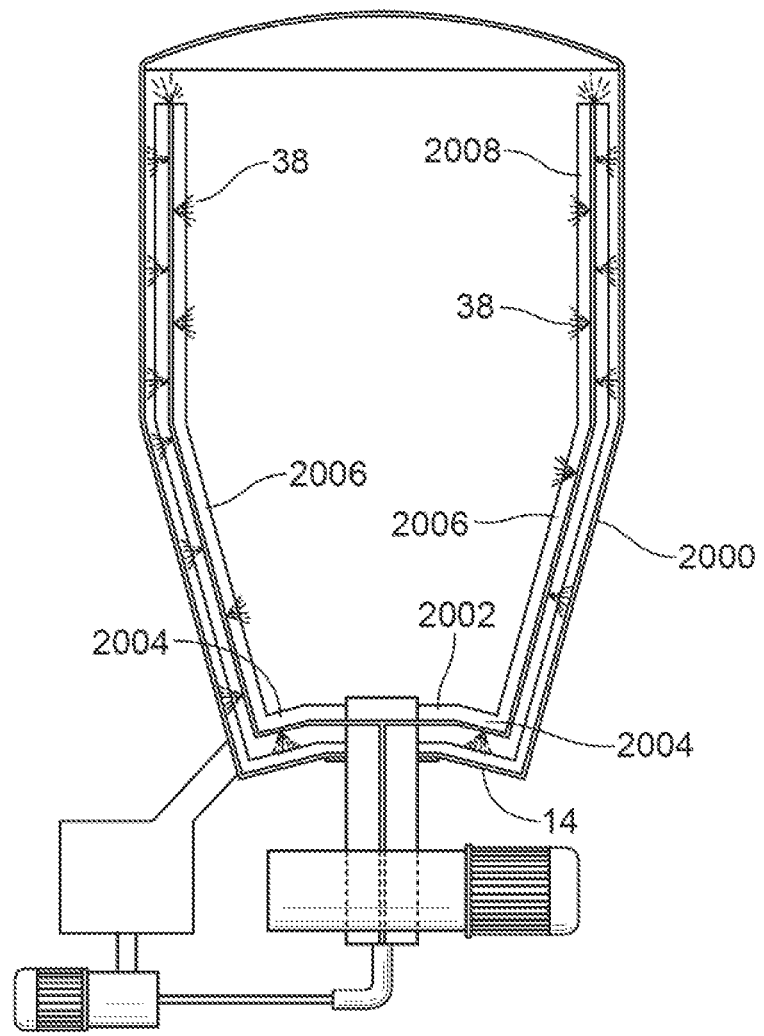

PROCESSING PAPER FEEDSTOCKS

RELATED APPLICATIONS

This application is a continuation application of U.S. application Ser. No. 13/396,365, filed Feb. 14, 2012, which claims priority to U.S. Provisional Application Ser. No. 61/442,710, filed Feb. 14, 2011. The complete disclosures of which are hereby incorporated by reference herein.

BACKGROUND

Magazines, catalogs, and other paper products that contain high levels of coatings, pigments, and inks, are widely available as waste materials. While efforts are made to recycle this waste paper, generally by repulping it for use in recycled paper products, it would be advantageous if this waste paper could be economically utilized as a feedstock to make other types of products.

SUMMARY

Generally, this invention relates to methods of processing paper feedstocks, and to intermediates and products made therefrom. In particular, the invention relates generally to the processing of certain types of relatively heavy paper feedstocks, such as highly pigmented papers, and or loaded papers, such as paper that has been color printed (printed with colors other than or in addition to black), e.g., magazines, and other papers.

Many of the methods disclosed herein utilize microorganisms or products produced by microorganisms, e.g., enzymes, to bioprocess the feedstock, producing useful intermediates and products, e.g., energy, fuels, foods and other materials. For example, in some cases enzymes are used to saccharify the feedstocks, converting the feedstocks to sugars. The sugars may be used as an end product or intermediate, or processed further, e.g., by fermentation. For example xylose can be hydrogenated to xylitol and glucose can be hydrogenated to sorbitol.

In one aspect, the invention features methods for producing a sugar, e.g., in the form of a solution or suspension, that includes providing a paper feedstock, the paper feedstock including offset printing paper e.g., offset printed paper, colored paper and/or coated paper e.g., polycoated paper and optionally mixing the feedstock with a fluid and/or saccharifying agent.

Some implementations include one or more of the following features. The paper feedstock may have a basis weight greater than 35 lb, e.g., from about 35 lb to 330 lb and/or the paper may have a high filler content, e.g., greater than about 10 wt. % e.g., greater than 20 wt. %. For example, the filler or any coating can be an inorganic material. The paper may also have a high grammage, e.g., greater than about 500 g/m$^2$. The paper may comprise a pigment or printing ink, e.g., at a level greater than about 0.025 wt. %. The paper can have an ash content greater than about 8 wt. %.

The method can further include adding a microorganism, for example a yeast and/or a bacteria (e.g., from the genus *Clostridium*), to the paper feedstock or saccharified paper and producing a product or intermediate.

The inventors have found that dispersion of a feedstock in a liquid mixture can be enhanced, and as a result the solids level of the mixture can be increased, by the use of certain mixing techniques and equipment. The mixing techniques and equipment disclosed herein also enhance mass transfer, and as a result reaction rates in a mixture, and avoid or minimize harm to sensitive ingredients of the mixture such as microorganisms and enzymes. In particular, jet mixing techniques, including for example jet aeration and jet flow agitation, have been found to provide good wetting, dispersion and mechanical disruption. By increasing the solids level of the mixture, the process can proceed more rapidly, more efficiently and more cost-effectively, and the resulting concentration of the final product can be increased.

Some of the processes disclosed herein include saccharification of a feedstock, and transportation of the feedstock from a remote location, e.g., where the feedstock is produced or stored, to the manufacturing facility. In some cases, saccharification can take place partially or entirely during transport. In such cases, it can be advantageous to provide mixing, e.g., jet mixing, in the transport vessel. In some cases, saccharification can be completed during transport. In some instances, fermentation can take place partially or entirely during transport.

In some implementations, the process further includes reducing the recalcitrance of a feedstock, before or during saccharification. The process may include the further steps of measuring the lignin content of the feedstock and determining whether pretreatment is needed and under what conditions based on the measured lignin content.

In one aspect, the invention features a method that includes saccharifying a biomass feedstock by mixing the feedstock with a liquid medium and a saccharifying agent in a vessel, using a jet mixer.

Some embodiments include one or more of the following features. The feedstock can have a bulk density of less than about 0.5 g/cm3. The feedstock may be, for example, a cellulosic or lignocellulosic material. The liquid can include water. The saccharifying agent can include an enzyme. The jet mixer may include, for example, a jet-flow agitator, a jet aeration type mixer, or a suction chamber jet mixer. If a jet aeration type mixer is used, it may be used without injection of air through the jet mixer. For example, if the jet aeration type mixer includes a nozzle having a first inlet line and a second inlet line, in some cases both inlet lines are supplied with a liquid. In some cases, mixing comprises adding the feedstock to the liquid medium in increments and mixing between additions. The method may further include monitoring the glucose level of the mixture of feedstock, liquid medium and saccharifying agent during mixing, and in some cases adding additional feedstock and saccharifying agent to the vessel during saccharification. The mixing vessel may be, for example, a tank, rail car or tanker truck. Saccharification can in some cases take place partially or completely during transport of the mixture of feedstock, liquid medium and saccharifying agent. The method may further include adding an emulsifier or surfactant to the mixture in the vessel.

In another aspect, the invention features saccharifying a biomass feedstock by mixing the feedstock with a liquid medium and a saccharifying agent in a vessel, using a mixer that produces generally toroidal flow within the vessel.

In some embodiments, the mixer is configured to limit any increase in the overall temperature of the liquid medium to less than 5° C. over the course of mixing. This aspect may also include, in some embodiments, any of the features discussed above.

In yet a further aspect, the invention features a method that includes converting a low molecular weight sugar to a product by mixing the low molecular weight sugar with a microorganism in a liquid medium, using a jet mixer.

Some embodiments include one or more of the following features. The liquid medium can include water. The microorganism can include yeast. The jet mixer can include a jet-flow agitator, jet aeration type mixer, or suction chamber jet mixer.

In another aspect, the invention features an apparatus that includes a tank, a jet mixer having a nozzle disposed within the tank, a delivery device configured to deliver a biomass feedstock to the tank, and a delivery device configured to deliver a metered amount of a saccharifying agent to the tank.

Some embodiments include one or more of the following features. The jet mixer can further include a motor, and the apparatus can further include a device configured to monitor the torque on the motor during mixing. The apparatus can also include a controller that adjusts the operation of the feedstock delivery device and/or the saccharifying agent delivery device based on input from the torque-monitoring device.

The invention also features a method that includes saccharifying a biomass feedstock in a vessel to form a saccharified mixture; inoculating the saccharified mixture in the vessel with a microorganism; and allowing the inoculated saccharified mixture to ferment in the vessel.

In some cases, the contents of the vessel are transferred to a transport vessel during fermentation and fermentation continues in the transport vessel. The method may further include agitating the contents of the vessel with a jet mixer during saccharification and fermentation. In some embodiments, the method further includes monitoring the oxygen content and ethanol and/or sugar content of the fermenting mixture.

The product can be a fuel, including, for example, alcohols (e.g., methanol, ethanol, propanol, isopropanol, erythritol, n-butanol, isobutanol, sec-butanol, tert-butanol, ethylene glycol, propylene glycol, 1,4-butane diol and/or glycerin), sugar alcohols (e.g., erythritol, glycol, glycerol, sorbitol threitol, arabitol, ribitol, mannitol, dulcitol, fucitol, iditol, isomalt, maltitol, lactitol, xylitol and other polyols), organic acids (e.g., formic acid, acetic acid, propionic acid, butyric acid, valeric acid, caproic acid, palmitic acid, stearic acid, oxalic acid, malonic acid, succinic acid, glutaric acid, oleic acid, linoleic acid, glycolic acid, lactic acid and/or γ-hydroxybutyric acid), hydrocarbons (methane, ethane, propane, isobutene, pentane, n-hexane, biodiesels and/or bio-gasolines), hydrogen and mixtures of these.

The method can further include adding a food-based nutrient source to the mixture, e.g., a nutrient source selected from the group consisting of grains, vegetables, residues of grains, residues of vegetables, and mixtures thereof, for example wheat, oats, barley, soybeans, peas, legumes, potatoes, corn, rice bran, corn meal, wheat bran, and mixtures thereof. In such cases, the mixture can further include an enzyme system selected to release nutrients from the food-based nutrient source, e.g., a system comprising a protease and an amylase.

The method can include detoxifying the sugar solution or suspension. The method can include further processing the sugar, for example, by separating xylose and or glucose from the sugar. In some cases, the saccharification can be conducted at a pH of about 3.8 to 4.2. The mixture can further include a nitrogen source.

In some cases, the method further includes physically treating the paper feedstock, for example mechanically treating to reduce the bulk density of the paper feedstock and/or increase the BET surface area of the feedstock. Physically treating the paper feedstock can include irradiation, for example, with an electron beam. The method can include mixing the paper feedstock with a fluid. The method can include detoxifying the paper feedstock, sugar, and/or other products or intermediates. The paper feedstock may be in the form of magazines. The paper feedstock may also be a laminate of at least one layer of a polymer and paper and may further include at least one layer of a metal e.g., aluminum.

Although many embodiments include the use of relatively heavy paper feedstocks, e.g., containing fillers and/or coatings other papers can be used e.g., newsprint.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 9 is a cross-sectional view of a jet aeration type mixer according to one embodiment.

FIGS. 19, 20, and 21-21A are views of various water jet devices that provide mixing while also minimizing hold up along the tank walls.

DETAILED DESCRIPTION

Using the methods and nutrient packages described herein, paper feedstocks that include high levels of pigments, colors, fillers and/or coatings, and/or that have a high basis weight, and the saccharified derivatives of such feedstocks, can be bioprocessed, e.g., using fermentation, to produce useful intermediates and products such as those described herein. In some cases, the feedstock includes high levels pigments and/or fillers such as those feedstocks used in printing, e.g., magazines. Examples of such feedstocks are described herein. Feedstocks of this type are advantageous for a number of reasons, including their relatively low cost (if waste materials are used) and, in the case of high basis weight papers, their relatively high density, which contributes to ease of handling and processing.

Converting Cellulosic and Lignocellulosic Materials to Alcohols

Figure 1:
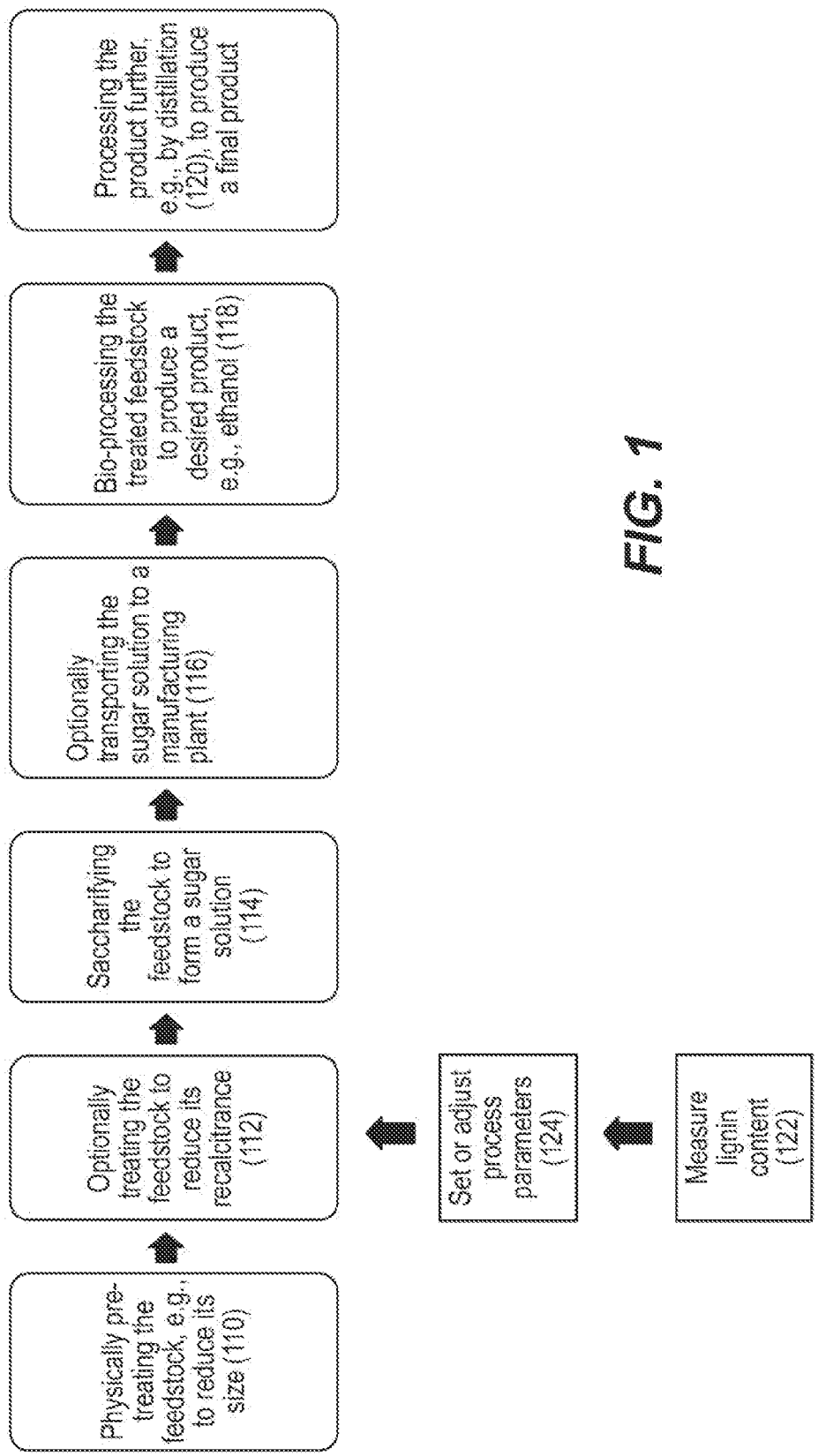
FIG. 1 is a flow diagram illustrating conversion of a feedstock to ethanol via production of a glucose solution.

Referring to FIG. 1, a process for manufacturing an alcohol, e.g., ethanol, or a butanol e.g., isobutanol, sec-butanol, tert-butanol or n-butanol, can include, for example, optionally mechanically treating the feedstock (step 110), before and/or after this treatment, optionally treating the feedstock with another physical treatment, for example irradiation, to further reduce its recalcitrance (step 112), saccharifying the feedstock to form a sugar solution (step 114), optionally transporting, e.g., by pipeline, railcar, truck or barge, the solution (or the feedstock, enzyme and water, if saccharification is performed en route) to a manufacturing plant (step 116), and then bio-processing the treated feedstock to produce a desired product (step 118), which is then processed further, e.g., by distillation (step 120). If desired, lignin content can be measured (step 122) and process parameters can be set or adjusted based on this measurement (step 124), as described in U.S. application Ser. No. 12/704,519, filed on Feb. 11, 2010, now U.S. Pat. No. 8,415,122, the complete disclosure of which is incorporated herein by reference.

Because paper feedstocks are generally low in, or entirely lack, nutrients to support bioprocesses, it is generally preferred that nutrients be added to the system, for example in the form of a food-based nutrient source or nutrient package, as disclosed in U.S. application Ser. No. 13/184,138, filed Jul. 15, 2011, now U.S. Pat. No. 8,852,901, incorporated by reference herein in its entirety. When utilized, the food-based nutrient source or nutrient package is present during bio-processing (step 118), e.g., fermentation, and may in some preferred implementations also be present during the saccharification step (step 114). In some implementations, the food-based nutrient source or nutrient package is added at the beginning of step 114, along with an enzyme combination suitable for saccharification, fermentation, and release of nutrients from the food-based nutrient source.

Saccharification is conducted under a first set of process conditions (e.g., temperature and pH), and then when saccharification has proceeded to a desired extent the process conditions may be adjusted (e.g., by adjusting pH from 4 to 5) to allow fermentation to proceed.

In some cases the feedstock includes materials that are not beneficial to the processing of the feedstock or decrease the quality of the intermediates and/or products. For example there may be materials that are toxic, and/or solid inorganic materials or insoluble organic materials. The toxic materials can be detrimental, for example, by reducing the effectiveness of enzymes and/or microorganisms. Examples of toxic materials are pigments and inks described herein. Solid inorganic materials can be detrimental, for example, in increasing the total viscosity and density of solutions in various processes as well as forming slurries, sludge and settled material that may, for example, block openings, be difficult to remove, e.g., from the bottom of tanks, and/or increase the wear on mixers. Examples of inorganic materials are fillers and coatings described herein. Insoluble organic materials can, for example, contaminate the final fuel products and/or cause foaming during mixing or other processing steps. Examples of insoluble organic materials are polymers used in polycoated paper described herein. It can therefore be advantageous to remove some of the insoluble solids and organic materials and to detoxify the feedstock at any point during the processing as described herein. Surprisingly, it has been found that in some cases materials in the feedstock that would be expected to be detrimental, as discussed above, do not significantly adversely affect the process. For example, some yeasts that provide ethanol by fermentation of sugars derived from paper feedstocks appear to be very resilient to various pigments, inks and fillers.

The manufacturing plant used in steps 118-120 (and in some cases all of the steps described above) can be, for example, an existing starch-based or sugar-based ethanol plant or one that has been retrofitted by removing or decommissioning the equipment upstream from the bio-processing system (which in a typical ethanol plant generally includes grain receiving equipment, a hammermill, a slurry mixer, cooking equipment and liquefaction equipment). In some cases, the feedstock received by the plant can be input directly into the fermentation equipment. A retrofitted plant is shown schematically in FIG. 2 and described below as well as, for example, in U.S. Ser. No. 12/429,045, filed Apr. 23, 2009, now U.S. Pat. No. 7,932,065, the complete disclosure of which is incorporated herein by reference.

Figure 2:
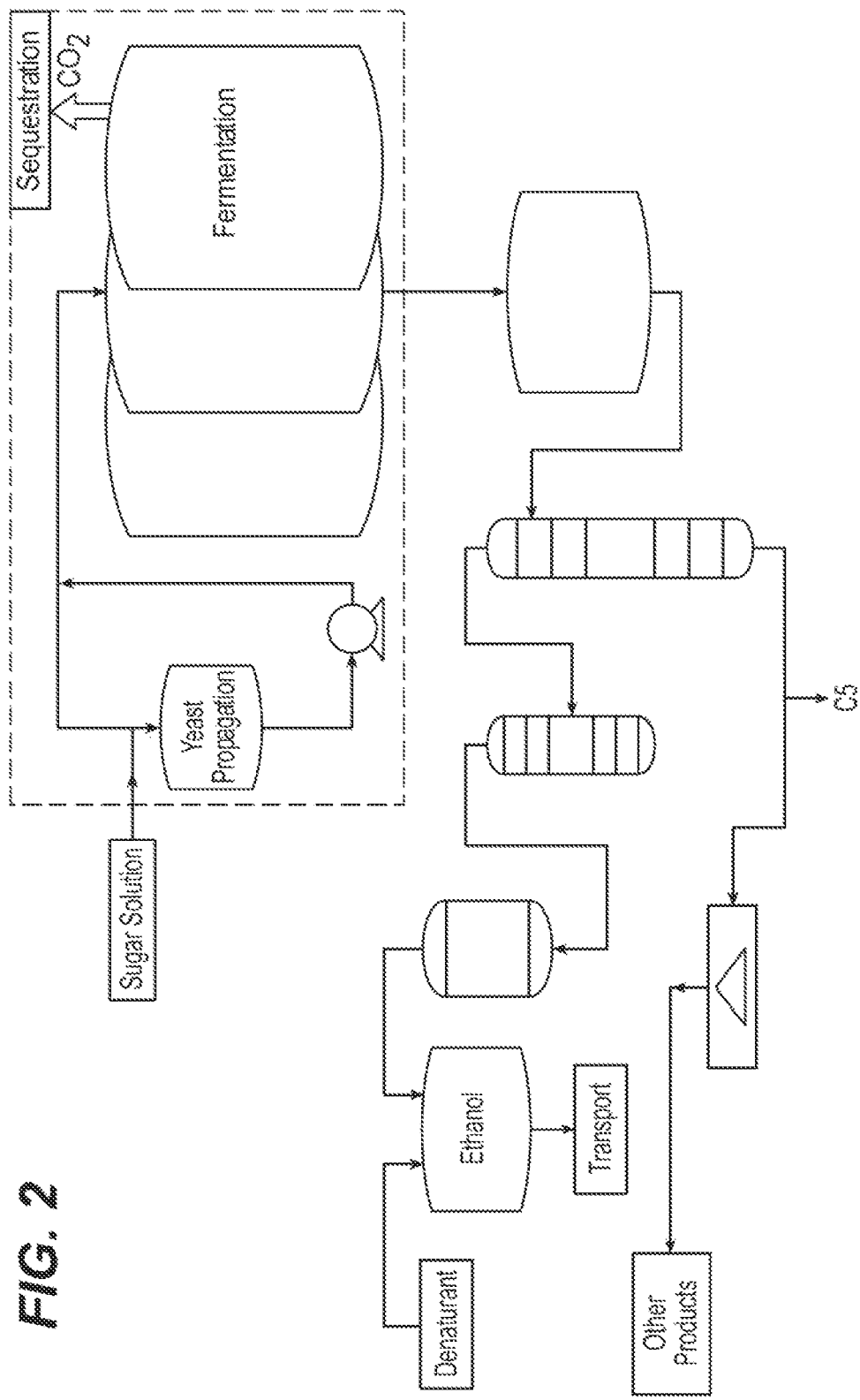
FIG. 2 is a schematic diagram of an ethanol manufacturing facility.

FIG. 2 shows one particular system that utilizes the steps described above for treating a feedstock and then using the treated feedstock in a fermentation process to produce an alcohol. System 100 includes a module 102 in which a feedstock is initially mechanically treated (step 12, above), a module 104 in which the mechanically treated feedstock is structurally modified (step 14, above), e.g., by irradiation, and a module 106 in which the structurally modified feedstock is subjected to further mechanical treatment (step 16, above). As discussed above, the module 106 may be of the same type as the module 102, or a different type. In some implementations the structurally modified feedstock can be returned to module 102 for further mechanical treatment rather than being further mechanically treated in a separate module 106. As described herein, many variations of system 100 can be utilized.

After these treatments, which may be repeated as many times as required to obtain desired feedstock properties, the treated feedstock is delivered to a fermentation system 108. Mixing may be performed during fermentation, in which case the mixing is preferably relatively gentle (low shear) so as to minimize damage to shear sensitive ingredients such as enzymes and other microorganisms. In some embodiments, jet mixing is used, as described in U.S. Ser. No. 12/782,694, filed May 18, 2010, now U.S. Pat. No. 8,636,402; U.S. Ser. No. 13/293,977, filed Nov. 10, 2011, now U.S. Pat. No. 8,669,099; and U.S. Ser. No. 13/293,985, filed Nov. 10, 2011, the complete disclosures of which are incorporated herein by reference. As disclosed in these documents, jet mixing may be conducted using a jet mixer that comprises a jet-flow agitator.

Referring again to FIG. 2, fermentation produces a crude ethanol mixture, which flows into a holding tank 110. Water or other solvent, and other non-ethanol components, are stripped from the crude ethanol mixture using a stripping column 112, and the ethanol is then distilled using a distillation unit 114, e.g., a rectifier. Distillation may be by vacuum distillation. Finally, the ethanol can be dried using a molecular sieve 116 and/or denatured, if necessary, and output to a desired shipping method.

In some cases, the systems described herein, or components thereof, may be portable, so that the system can be transported (e.g., by rail, truck, or marine vessel) from one location to another. The method steps described herein can be performed at one or more locations, and in some cases one or more of the steps can be performed in transit. Such mobile processing is described in U.S. Ser. No. 12/374,549, filed Jul. 20, 2007, now U.S. Pat. No. 8,318,453; and International Application No. WO 2008/011598, the full disclosures of which are incorporated herein by reference.

Any or all of the method steps described herein can be performed at ambient temperature. If desired, cooling and/or heating may be employed during certain steps. For example, the feedstock may be cooled during mechanical treatment to increase its brittleness. In some embodiments, cooling is employed before, during or after the initial mechanical treatment and/or the subsequent mechanical treatment. Cooling may be performed as described in U.S. Ser. No. 12/502,629, filed Jul. 14, 2009, now U.S. Pat. No. 7,900,857, the full disclosure of which is incorporated herein by reference. Moreover, the temperature in the fermentation system 108 may be controlled to enhance saccharification and/or fermentation.

The individual steps of the methods described above, as well as the materials used, will now be described in further detail.

Mixing Feedstock, Enzyme and Liquid

The processes disclosed herein can utilize low bulk density materials, for example cellulosic or lignocellulosic feedstocks that have been physically pretreated to have a bulk density of less than about 0.5 g/cm3, e.g., less than about 0.35 g/cm3, 0.25 g/cm3, 0.20 g/cm3, 0.15 g/cm3, 0.10 g/cm3, 0.05 g/cm3 or less, e.g., 0.025 g/cm3.

Such materials can be especially difficult to mix with liquids, e.g., with water or a solvent system for saccharification, fermentation, or other processing. Due to their low bulk density, the materials tend to float to the surface of the liquid rather than being dispersed therein. In some cases, the materials can be hydrophobic, highly crystalline, or otherwise difficult to wet. At the same time, it is desirable to process the feedstock in a relatively high solids level dispersion, in order to obtain a high final concentration of sugar in the saccharified material, or a high concentration of the desired product after processing (e.g., of ethanol or other alcohol(s) after fermentation). In some cases, utilizing the methods described herein the solids level of the dispersion during processing can be, for example, at least 20, 25, 30, 35, 40, 45, or even at least 50 percent by weight dissolved solids.

The inventors have found that dispersion of a feedstock in a liquid mixture can be enhanced, and as a result the solids level of the mixture can be increased, by the use of certain mixing techniques and equipment. The mixing techniques and equipment disclosed herein also enhance mass transfer, and as a result reaction rates in a mixture, and avoid or minimize harm to sensitive ingredients of the mixture such as microorganisms and enzymes. In particular, jet mixing techniques, including for example jet aeration and jet flow agitation, have been found to provide good wetting, dispersion and mechanical disruption. By increasing the solids level of the mixture, the process can proceed more rapidly, more efficiently and more cost-effectively, and the resulting concentration of the final product can be increased.

Mixing Characteristics

Various types of mixing devices are described below, and other mixing devices may be used. Suitable mixers have in common that they produce high velocity circulating flow, for example flow in a toroidal or elliptical pattern. Generally, preferred mixers exhibit a high bulk flow rate. Preferred mixers provide this mixing action with relatively low energy consumption. It is also generally preferred that the mixer produce relatively low shear and avoid heating of the liquid medium, as shear and/or heat can deleteriously affect the saccharifying agent (or microorganism, e.g., in the case of fermentation). As will be discussed in detail below, some preferred mixers draw the mixture through an inlet into a mixing element, which may include a rotor or impeller, and then expel the mixture from the mixing element through an outlet nozzle. This circulating action, and the high velocity of the jet exiting the nozzle, assist in dispersing material that is floating on the surface of the liquid or material that has settled to the bottom of the tank, depending on the orientation of the mixing element. Mixing elements can be positioned in different orientations to disperse both floating and settling material, and the orientation of the mixing elements can in some cases be adjustable.

In some preferred mixing systems the velocity $v_o$ of the jet as it meets the ambient fluid is from about 2 to 300 m/s, e.g., about 5 to 150 m/s or about 10 to 100 m/s. The power consumption of the mixing system may be about 20 to 1000 KW, e.g., 30 to 570 KW or 50 to 500 KW, or 150 to 250 KW for a 100,000 L tank. It is generally preferred that the power usage be low for cost-effectiveness.

Jet Mixing

Jet mixing involves the discharge of a submerged jet, or a number of submerged jets, of high velocity liquid into a fluid medium, in this case the mixture of biomass feedstock, liquid medium and saccharifying agent. The jet of liquid penetrates the fluid medium, with its energy being dissipated by turbulence and some initial heat. This turbulence is associated with velocity gradients (fluid shear). The surrounding fluid is accelerated and entrained into the jet flow, with this secondary entrained flow increasing as the distance from the jet nozzle increases. The momentum of the secondary flow remains generally constant as the jet expands, as long as the flow does not hit a wall, floor or other obstacle.

Figure 3:
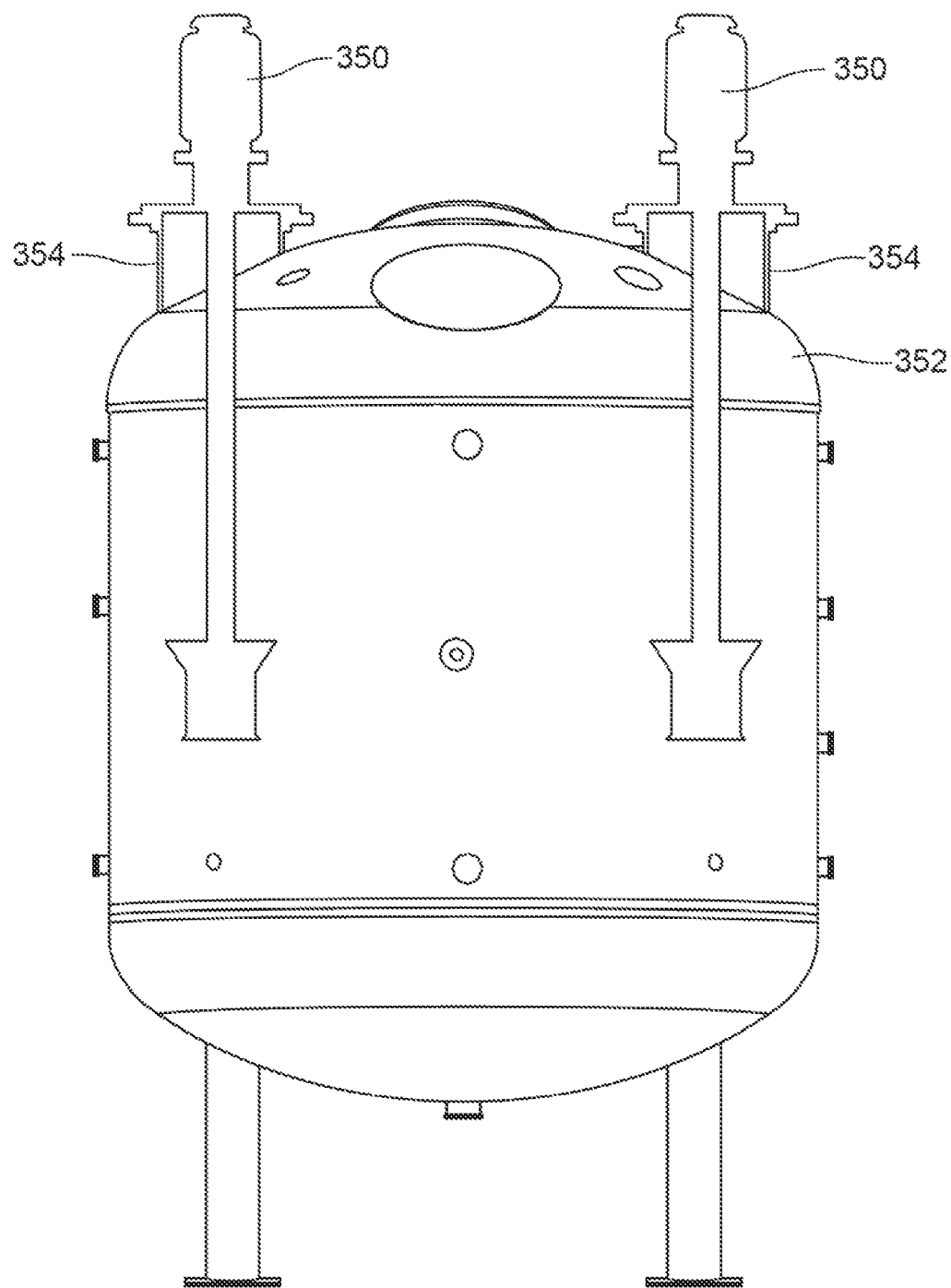
FIG. 3 is a cross-sectional view of a tank having a domed bottom and two jet mixers extending into the tank from above.

The longer the flow continues before it hits any obstacle, the more liquid is entrained into the secondary flow, increasing the bulk flow in the tank or vessel. When it encounters an obstacle, the secondary flow will lose momentum, more or less depending on the geometry of the tank, e.g., the angle at which the flow impinges on the obstacle. It is generally desirable to orient the jets and/or design the tank so that hydraulic losses to the tank walls are minimized. For example, it may be desirable for the tank to have an arcuate bottom (e.g., a domed headplate), and for the jet mixers to be oriented relatively close to the sidewalls, as shown in FIG. 3. The tank bottom (lower head plate) may have any desired domed configuration, or may have an elliptical or conical geometry.

Jet mixing differs from most types of liquid/liquid and liquid/solid mixing in that the driving force is hydraulic rather than mechanical. Instead of shearing fluid and propelling it around the mixing vessel, as a mechanical agitator does, a jet mixer forces fluid through one or more nozzles within the tank, creating high-velocity jets that entrain other fluid. The result is shear (fluid against fluid) and circulation, which mix the tank contents efficiently.

Figure 4:
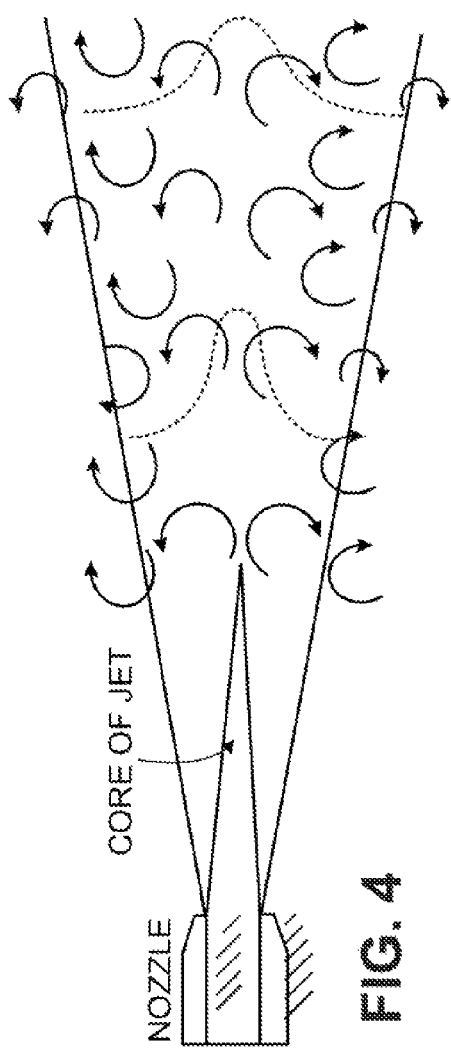
FIGS. 4 and 4A are diagrams illustrating jet flow exiting a nozzle.
Figure 4A:
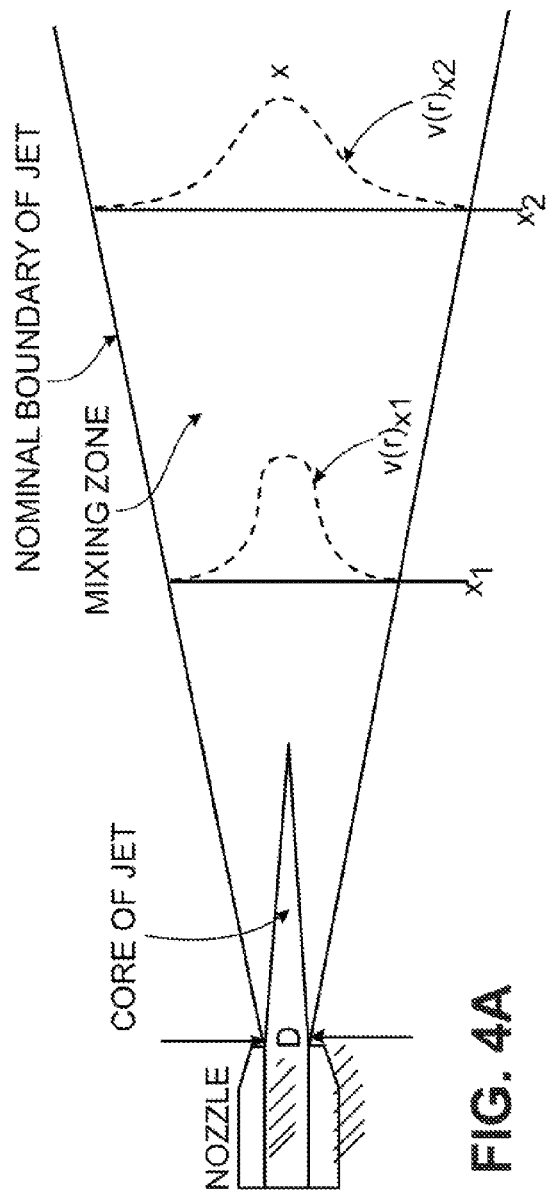

Referring to FIG. 4, the high velocity gradient between the core flow from a submerged jet and the surrounding fluid causes eddies. FIG. 4A illustrates the general characteristics of a submerged jet. As the submerged jet expands into the surrounding ambient environment the velocity profile flattens as the distance (x) from the nozzle increases. Also, the velocity gradient dv/dr changes with r (the distance from the centerline of the jet) at a given distance x, such that eddies are created which define the mixing zone (the conical expansion from the nozzle).

In an experimental study of a submerged jet in air (the results of which are applicable to any fluid, including water), Albertson et al. ("Diffusion of Submerged Jets," Paper 2409, Amer. Soc. of Civil Engineers Transactions, Vol. 115:639-697, 1950, at p. 657) developed dimensionless relationships for $v(x)r=0/v_o$ (centerline velocity), $v(r)x/v(x)r=0$ (velocity profile at a given x), $Q_x/Q_o$ (flow entrainment), and $E_x/E_o$ (energy change with x):

(1) Centerline velocity, $v(x)$ $r=0/v_o$:

$$\frac{v(r=0)}{v_o} \frac{x}{D_o} = 6.2$$

(2) velocity profile at any x, $v(r)x/v(x)r=0$:

$$\log\left[\frac{v(r)_x}{v_o} \frac{x}{D_o}\right] = 0.79 - 33\frac{r^2}{x^2}$$

(3) Flow and energy at any x:

$$\frac{Q_x}{Q_o} = 0.32 \frac{x}{D_o}$$

$$\frac{E_x}{E_o} = 4.1 \frac{D_o}{x}$$

where:
$v(r=0)$=centerline velocity of submerged jet (m/s),
$v_o$=velocity of jet as it emerges from the nozzle (m/s),
x=distance from nozzle (m),
r=distance from centerline of jet (m),
$D_o$=diameter of nozzle (m),
$Q_x$=flow of fluid across any given plane at distance x from the nozzle (me/s),
$Q_o$=flow of fluid emerging from the nozzle (m3/s),
E=energy flux of fluid across any given plane at distance x from the nozzle (m3/s),
$E_o$=energy flux of fluid emerging from the nozzle (m3/s).
("Water Treatment Unit Processes: Physical and Chemical," David W. Hendricks, CRC Press 2006, p. 411.)

Jet mixing is particularly cost-effective in large-volume (over 1,000 gal) and low-viscosity (under 1,000 cPs) applications. It is also generally advantageous that in most cases the pump or motor of the jet mixer not be submerged, e.g., when a pump is used it is generally located outside the vessel.

One advantage of jet mixing is that the temperature of the ambient fluid (other than directly adjacent the exit of the nozzle, where there may be some localized heating) is increased only slightly if at all. For example, the temperature may be increased by less than 5° C., less than 1° C., or not to any measurable extent.

Jet-Flow Agitators

Figure 5:
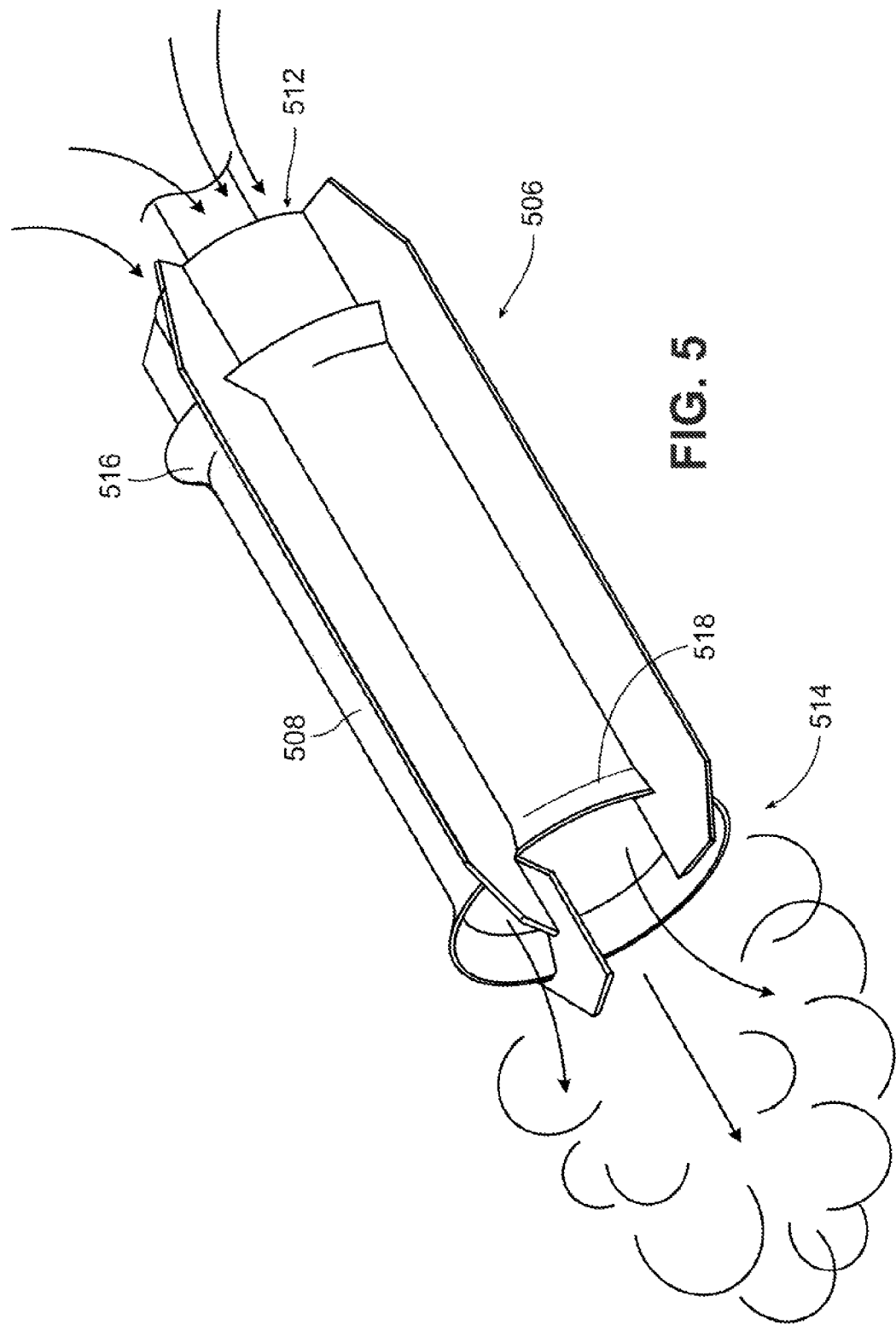
FIG. 5 is a diagrammatic perspective view of a jet-flow agitator according to one embodiment.
Figure 5A:
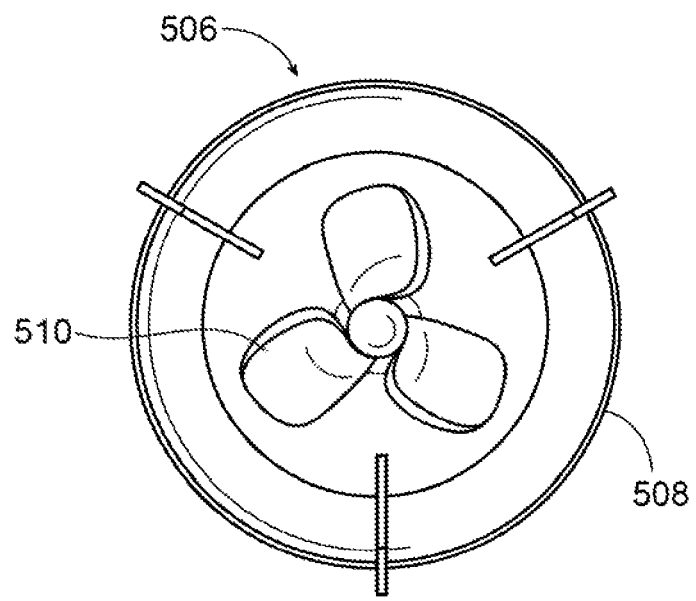
FIG. 5A is an enlarged perspective view of the impeller and jet tube of the jet-flow agitator of FIG. 5.

One type of jet-flow agitator is shown in FIGS. 5-5A. This type of mixer is available commercially, e.g., from IKA under the tradename ROTOTRON™. Referring to FIG. 5, the mixer includes a motor, which rotates a drive shaft. A mixing element 506 is mounted at the end of the drive shaft. As shown in FIG. 5A, the mixing element 506 includes a shroud 508 and, within the shroud, an impeller 510. As indicated by the arrows, when the impeller is rotated in its "forward" direction, the impeller 510 draws liquid in through the open upper end 512 of the shroud and forces the liquid out through the open lower end 514. Liquid exiting end 514 is in the form of a high velocity stream or jet. If the direction of rotation of the impeller 510 is reversed, liquid can be drawn in through the lower end 514 and ejected through the upper end 512. This can be used, for example, to suck in solids that are floating near or on the surface of the liquid in a tank or vessel. (It is noted that "upper" and "lower" refer to the orientation of the mixer in FIG. 5; the mixer may be oriented in a tank so that the upper end is below the lower end.)

The shroud 508 includes flared areas 516 and 518 adjacent its ends. These flared areas are believed to contribute to the generally toroidal flow that is observed with this type of mixer. The geometry of the shroud and impeller also concentrate the flow into a high velocity stream using relatively low power consumption.

Preferably, the clearance between the shroud 508 and the impeller 510 is sufficient so as to avoid excessive milling of the material as it passes through the shroud. For example, the clearance may be at least 10 times the average particle size of the solids in the mixture, preferably at least 100 times.

In some implementations, the shaft is configured to allow gas delivery through the shaft. For example, the shaft may include a bore (not shown) through which gas is delivered, and one or more orifices through which gas exits into the mixture. The orifices may be within the shroud 508, to enhance mixing, and/or at other locations along the length of the shaft.

Figure 5B:
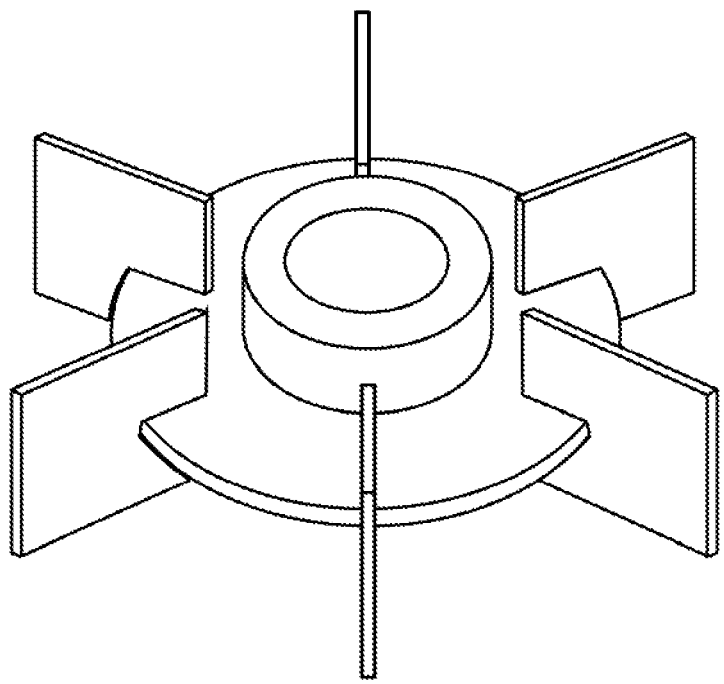
FIG. 5B is an enlarged perspective view of an alternate impeller.

The impeller 510 may have any desired geometry that will draw liquid through the shroud at a high velocity. The impeller is preferably a marine impeller, as shown in FIG. 5A, but may have a different design, for example, a Rushton impeller as shown in FIG. 5B, or a modified Rushton impeller, e.g., tilted so as to provide some axial flow.

In order to generate the high velocity flow through the shroud, the motor is preferably a high speed, high torque motor, e.g., capable of operating at 500 to 20,000 RPM, e.g., 3,000 to 10,000 RPM. However, the larger the mixer (e.g., the larger the shroud and/or the larger the motor) the lower the rotational speed can be. Thus, if a large mixer is used, such as a 5 hp, 10 hp, 20 hp, or 30 hp or greater, the motor may be designed to operate at lower rotational speeds, e.g., less than 2000 RPM, less than 1500 RPM, or even 500 RPM or less. For example, a mixer sized to mix a 10,000-20,000 liter tank may operate at speeds of 900 to 1,200 RPM. The torque of the motor is preferably self-adjusting, to maintain a relatively constant impeller speed as the mixing conditions change over time, e.g., due to saccharification of the solids.

Advantageously, the mixer can be oriented at any desired angle or location in the tank, to direct the jet flow in a desired direction. Moreover, as discussed above, depending on the direction of rotation of the impeller the mixer can be used to draw fluid from either end of the shroud.

In some implementations, two or more jet mixers are positioned in the vessel, with one or more being configured to jet fluid upward ("up pump") and one or more being configured to jet fluid downward ("down pump"). In some cases, an up pumping mixer will be positioned adjacent a down pumping mixer, to enhance the turbulent flow created by the mixers. If desired, one or more mixers may be switched between upward flow and downward flow during processing. It may be advantageous to switch all or most of the mixers to up pumping mode during initial dispersion of the feedstock in the liquid medium, particularly if the feedstock is dumped or blown onto the surface of the liquid, as up pumping creates significant turbulence at the surface. Up pumping can also be used during fermentation to help remove $CO_2$ from the liquid by causing the gas to bubble to the surface where it can be vented.

Suction Chamber Jet Mixers

Another type of jet mixer includes a primary nozzle that delivers a pressurized fluid from a pump, a suction inlet adjacent the primary nozzle through which ambient fluid is drawn by the pressure drop between the primary nozzle and the wider inlet, and a suction chamber extending between the suction inlet and a secondary nozzle. A jet of high velocity fluid exits the secondary nozzle.

Figure 6:
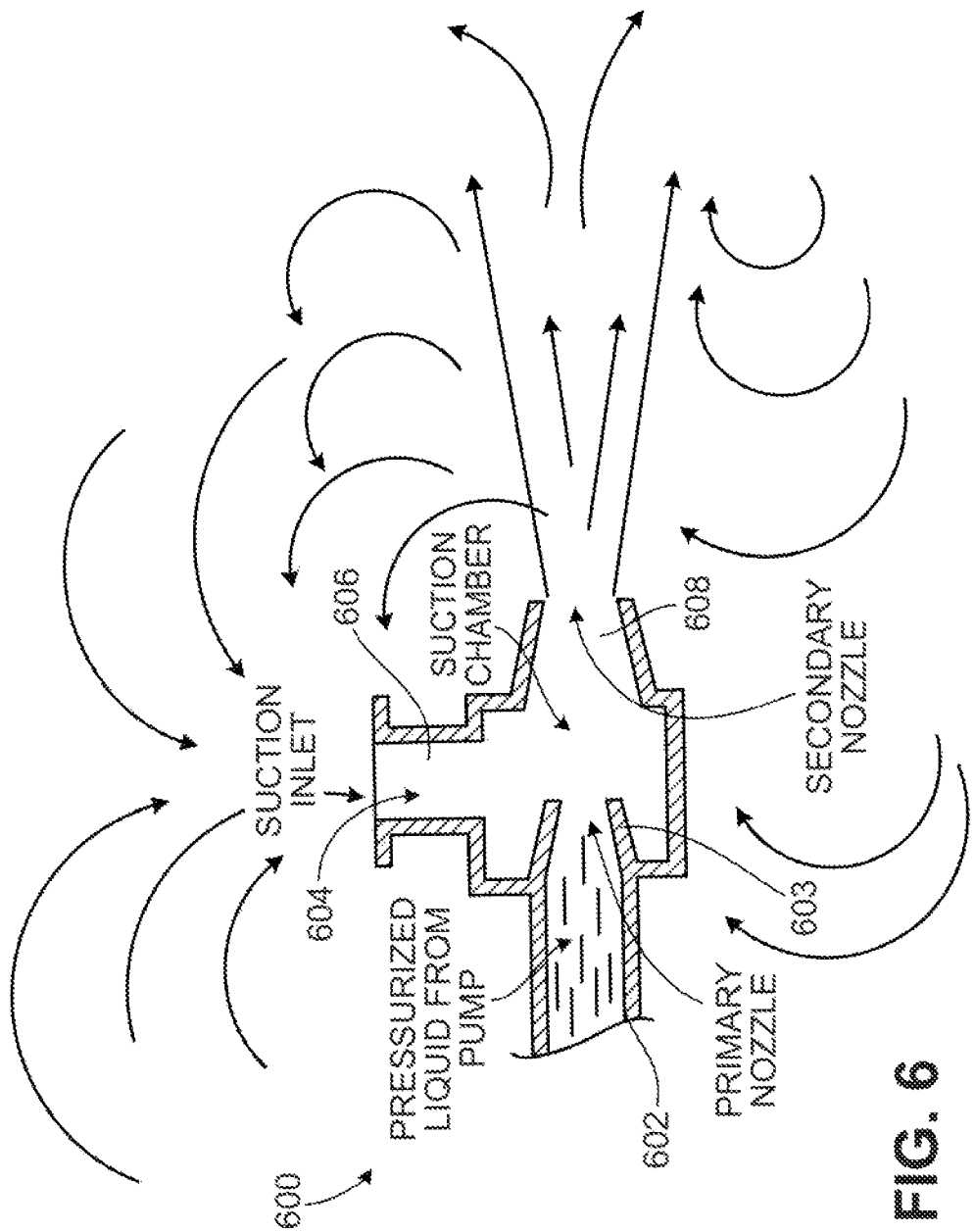
FIG. 6 is a diagram of a suction chamber jet mixing nozzle according to one embodiment.

An example of this type of mixer is shown in FIG. 6. As shown, in mixer 600 pressurized liquid from a pump (not shown) flows through an inlet passage 602 and exits through a primary nozzle 603. Ambient liquid is drawn through a suction inlet 604 into suction chamber 606 by the pressure drop caused by the flow of pressurized liquid. The combined flow exits from the suction chamber into the ambient liquid at high velocity through secondary nozzle 608. Mixing occurs both in the suction chamber and in the ambient liquid due to the jet action of the exiting jet of liquid.

Figure 6A:
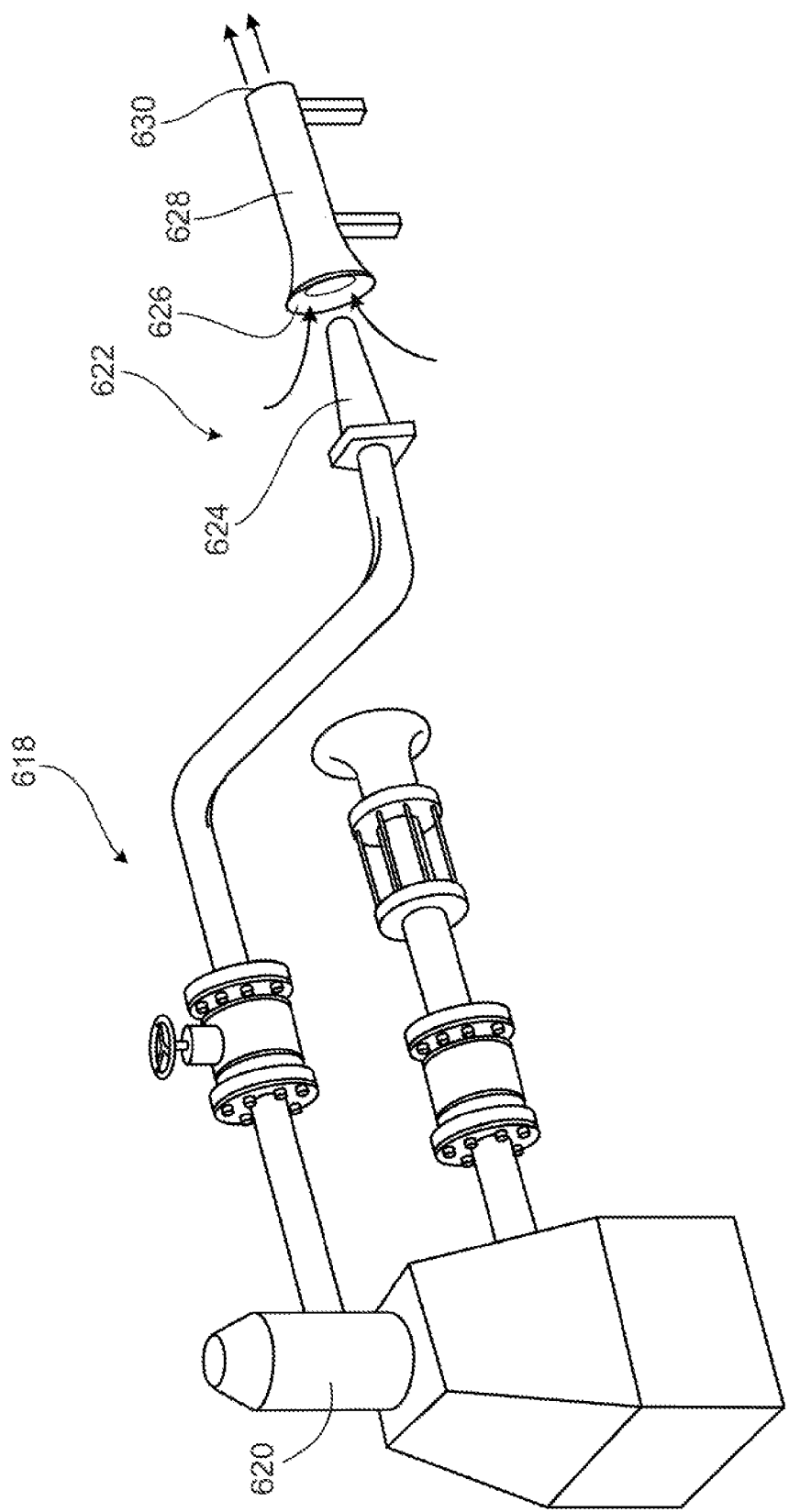
FIG. 6A is a perspective view of a suction chamber jet mixing system according to another embodiment.

A mixing system that operates according to a similar principle is shown in FIG. 6A. Mixers embodying this design are commercially available from ITT Water and Wastewater, under the tradename FLYGT™ jet mixers. In system 618, pump 620 generates a primary flow that is delivered to the tank (not shown) through a suction nozzle system 622. The suction nozzle system 622 includes a primary nozzle 624 which functions in a manner similar to primary nozzle 603 described above, causing ambient fluid to be drawn into the adjacent open end 626 of ejector tube 628 due to the pressure drop induced by the fluid exiting the primary nozzle. The combined flow then exits the other end 630 of ejector tube 628, which functions as a secondary nozzle, as a high velocity jet.

Figure 7:
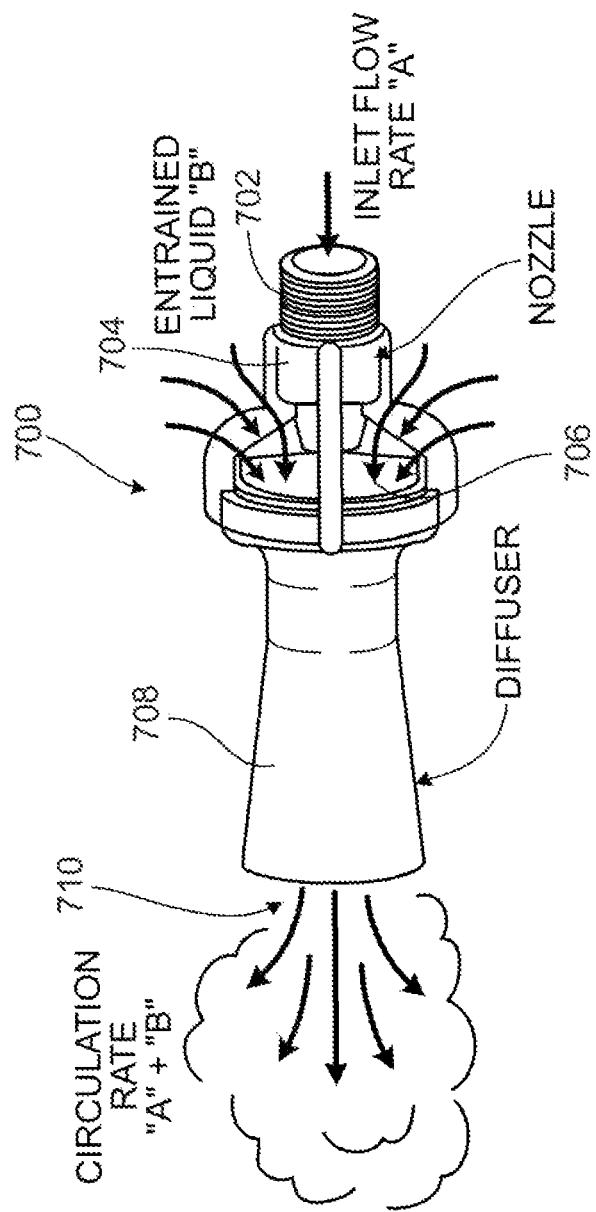
FIG. 7 is a diagrammatic perspective view of a jet mixing nozzle for a suction chamber jet mixing system according to another alternate embodiment.

The nozzle shown in FIG. 7, referred to as an eductor nozzle, operates under a similar principle. A nozzle embodying this design is commercially available under the tradename TEEJET®. As shown, in nozzle 700 pressurized liquid flows in through an inlet 702 and exits a primary nozzle 704, drawing ambient fluid in to the open end 706 of a diffuser 708. The combined flow exits the opposite open end 710 of the diffuser at a circulation flow rate A+B that is the sum of the inlet flow rate A and the flow rate B of the entrained ambient fluid.

Jet Aeration Type Mixers

Another type of jet mixing system that can be utilized is referred to in the wastewater industry as "jet aeration mixing." In the wastewater industry, these mixers are typically used to deliver a jet of a pressurized air and liquid mixture, to provide aeration. However, in the present application in some cases the jet aeration type mixers are utilized without pressurized gas, as will be discussed below. The principles of operation of jet aeration mixers will be initially described in the context of their use with pressurized gas, for clarity.

Figure 8:
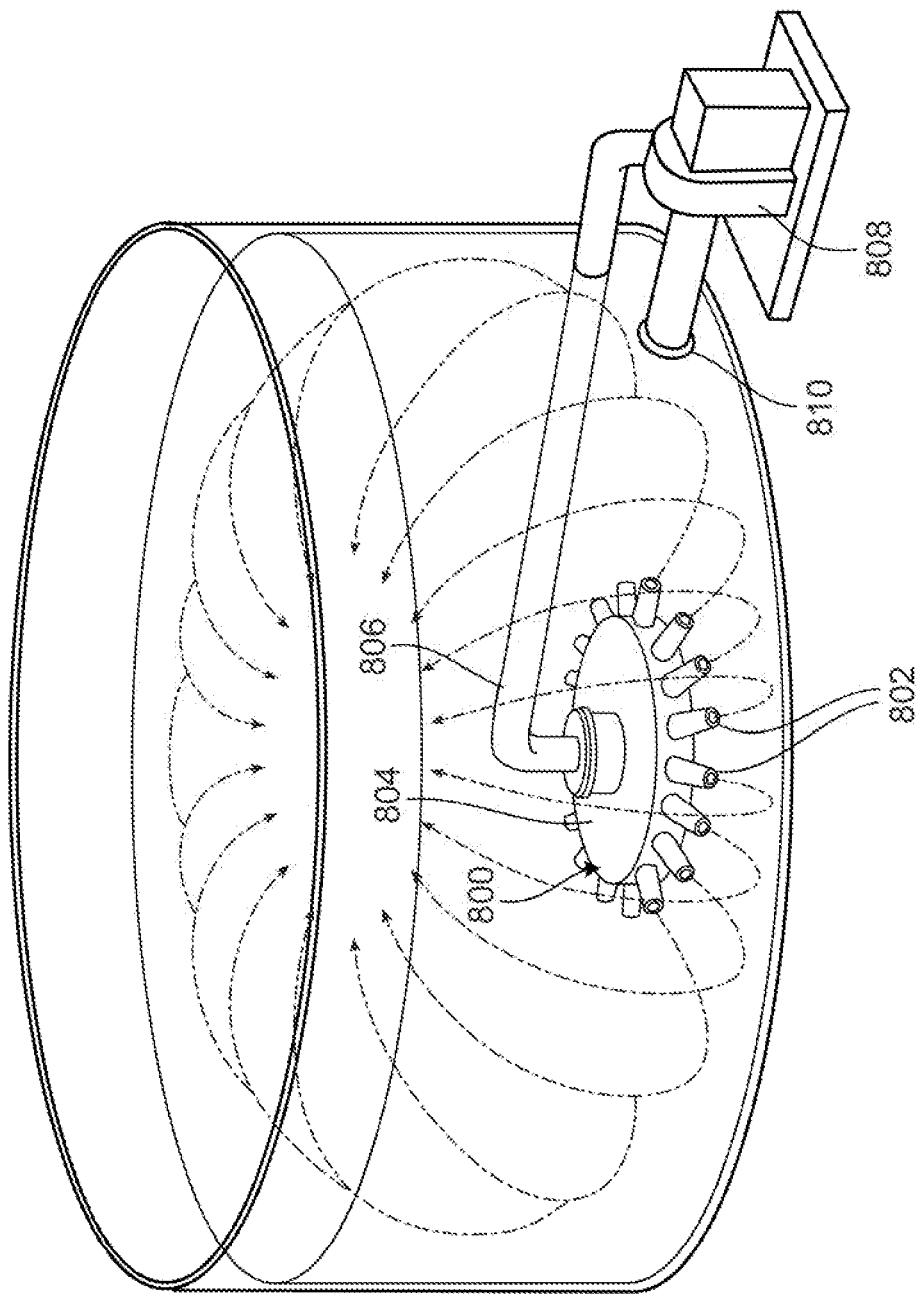
FIG. 8 is a diagrammatic perspective view of a tank and a jet aeration type mixing system positioned in the tank, with the tank being shown as transparent to allow the jet mixer and associated piping to be seen.
Figure 8A:
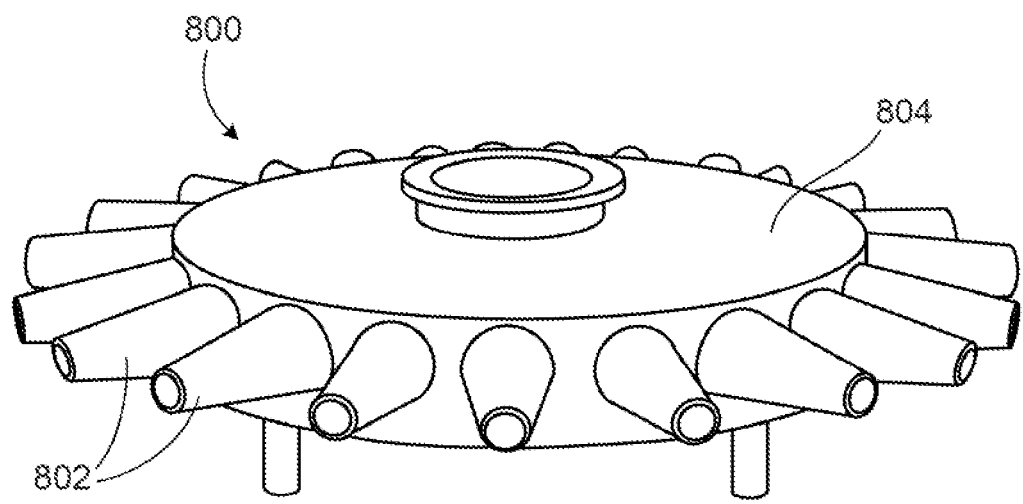
FIG. 8A is a perspective view of the jet mixer used in the jet aeration system of FIG. 8.
Figure 8B:
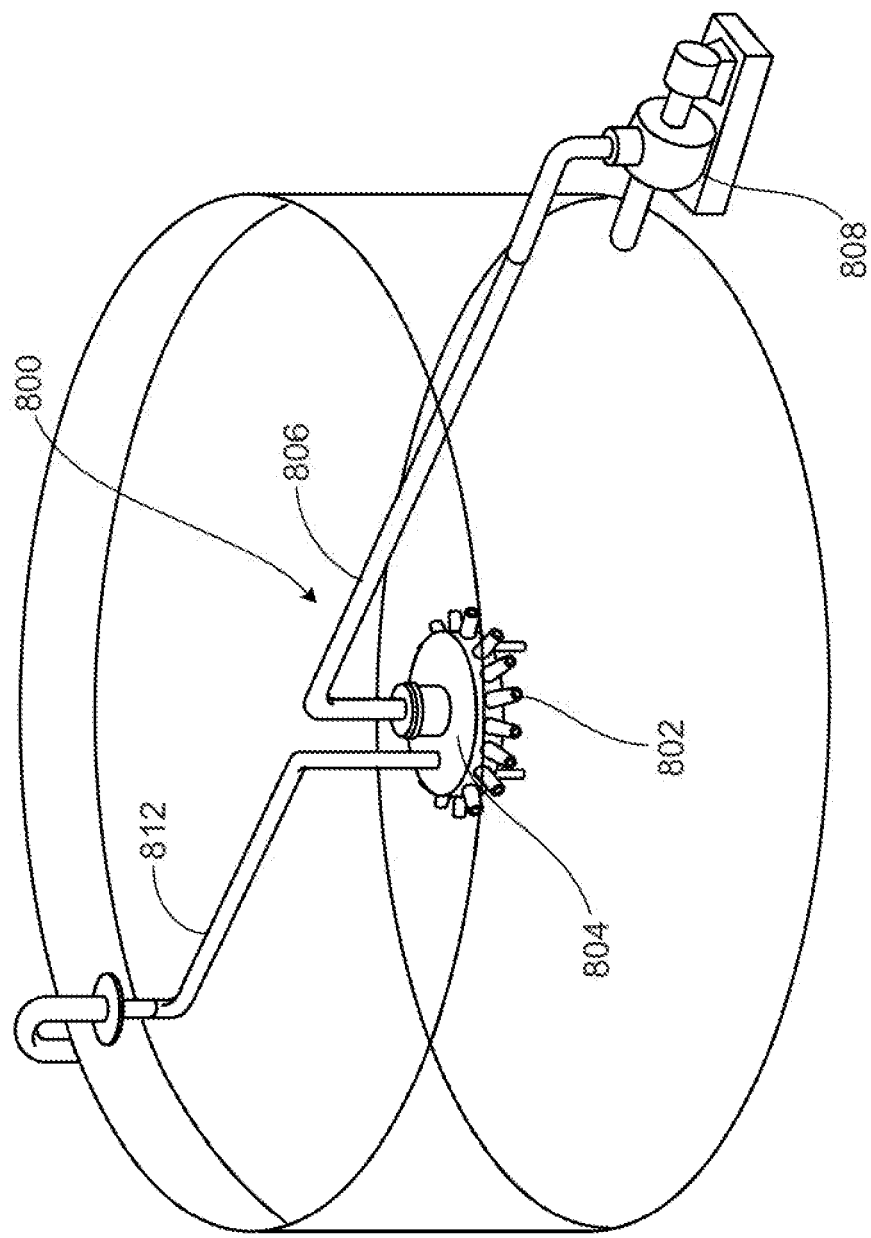
FIG. 8B is a diagrammatic perspective view of a similar system in which an air intake is provided.

An eddy jet mixer, such as the mixer 800 shown in FIGS. 8-8B, includes multiple jets 802 mounted in a radial pattern on a central hub 804. The radial pattern of the jets uniformly distributes mixing energy throughout the tank. The eddy jet mixer may be centrally positioned in a tank, as shown, to provide toroidal flow about the center axis of the tank. The eddy jet mixer may be mounted on piping 806, which supplies high velocity liquid to the eddy jet mixer. In the embodiment shown in FIG. 8B, air is also supplied to the eddy jet mixer through piping 812. The high velocity liquid is delivered by a pump 808 which is positioned outside of the tank and which draws liquid in through an inlet 810 in the side wall of the tank.

Figure 10:
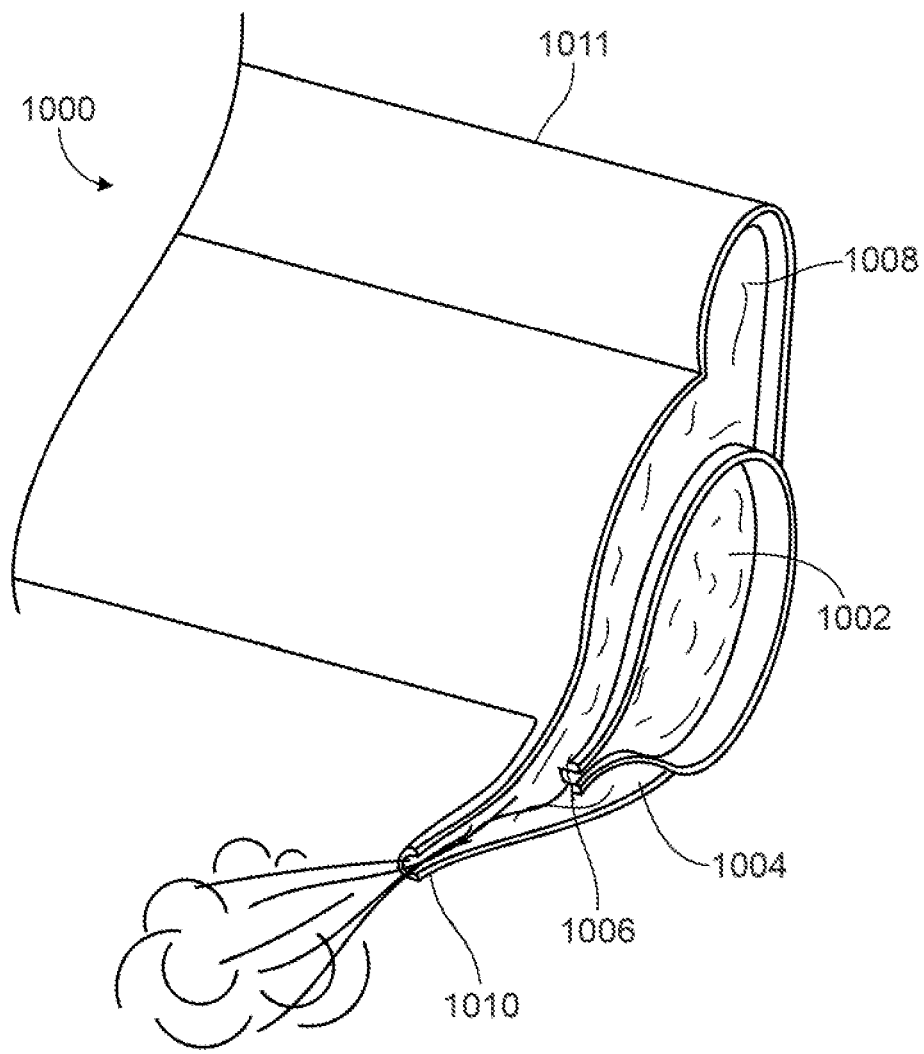
FIG. 10 is a cross-sectional view of a jet aeration type mixer according to an alternate embodiment.

FIGS. 9 and 10 show two types of nozzle configurations that are designed to mix a gas and a liquid stream and eject a high velocity jet. These nozzles are configured somewhat differently from the eddy jet mixer shown in FIGS. 8 and 8A but function in a similar manner. In the system 900 shown in FIG. 9, a primary or motive fluid is directed through a liquid line 902 to inner nozzles 904 through which the liquid travels at high velocity into a mixing area 906. A second fluid, e.g., a gas, such as compressed air, nitrogen or carbon dioxide, or a liquid, enters the mixing area through a second line 908 and entrained in the motive fluid entering the mixing area 906 through the inner nozzles. In some instances the second fluid is nitrogen or carbon dioxide so as to reduce oxidation of the enzyme. The combined flow from the two lines is jetted into the mixing tank through the outer nozzles 910. If the second fluid is a gas, tiny bubbles are entrained in the liquid in the mixture. Liquid is supplied to the liquid line 902 by a pump. Gas, if it is used, is provided by compressors. If a liquid is used as the second fluid, it can have the same velocity as the liquid entering through the liquid line 902, or a different velocity.

FIG. 10 shows an alternate nozzle design 1000, in which outer nozzles 1010 (of which only one is shown) are positioned along the length of an elongated member 1011 that includes a liquid line 1002 that is positioned parallel to a second line 1008. Each nozzle includes a single outer nozzle 1010 and a single inner nozzle 1004. Mixing of the motive liquid with the second fluid proceeds in the same manner as in the system 900 described above.

Figure 11:
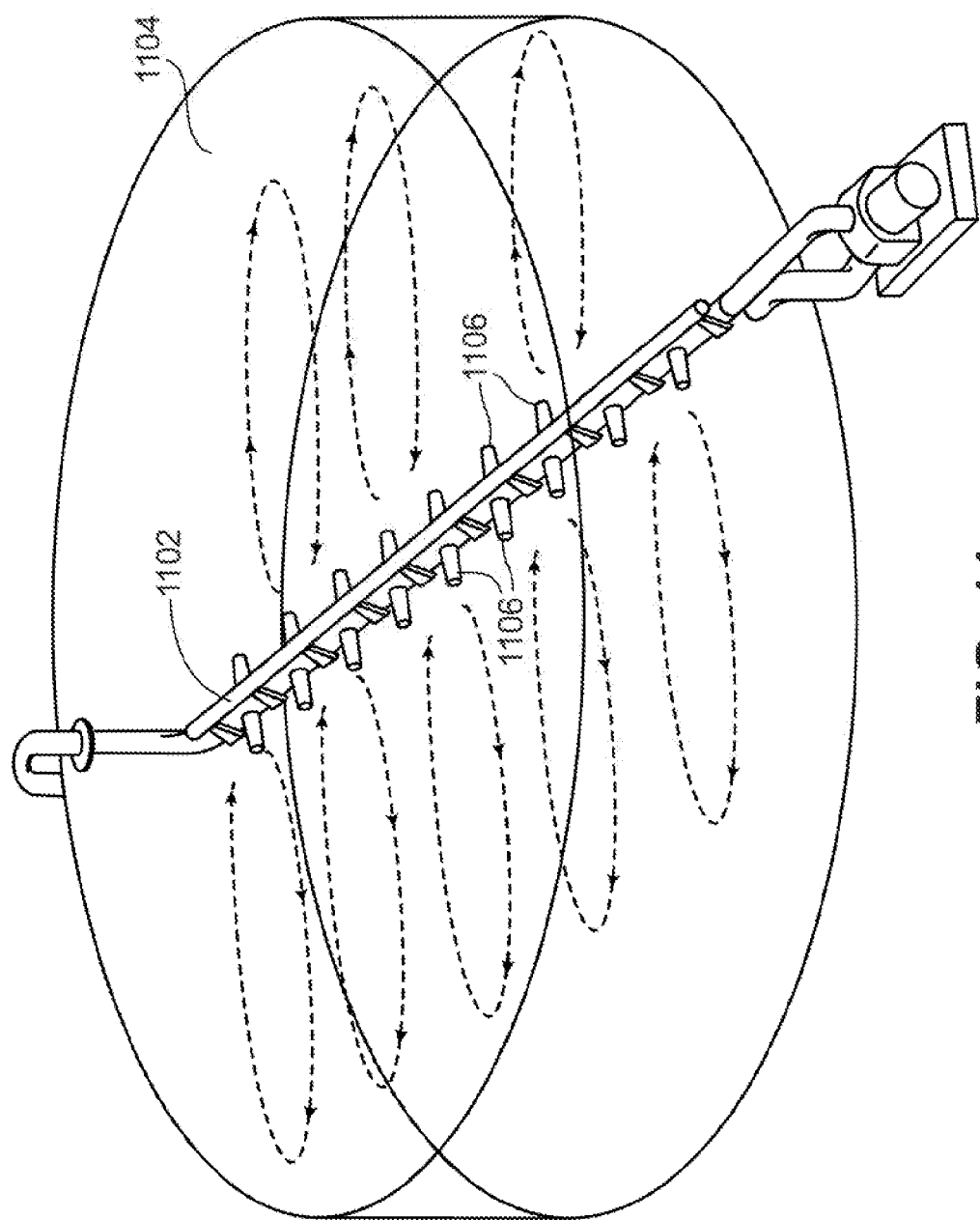
FIGS. 11-13 are diagrams illustrating alternative flow patterns in tanks containing different configurations of jet mixers.
Figure 12:
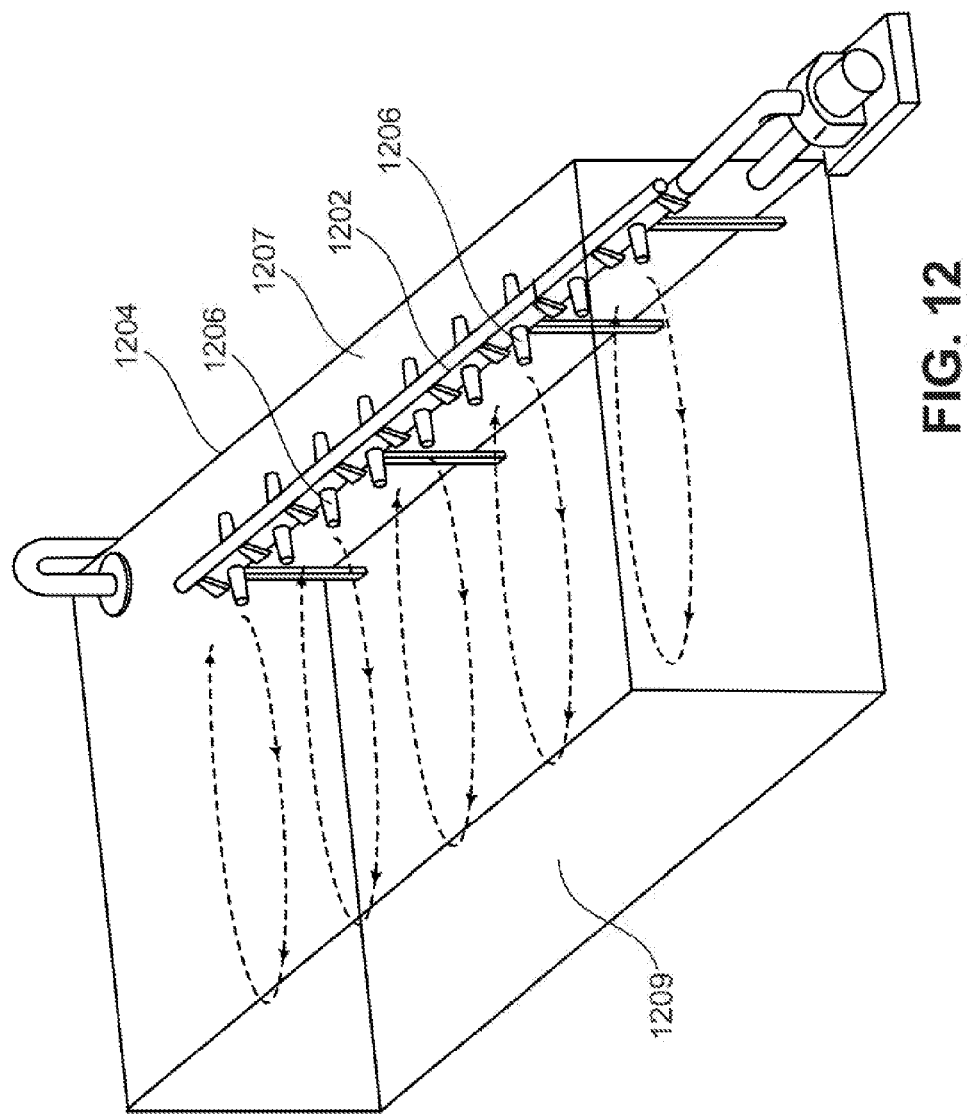

FIGS. 11 and 12 illustrate examples of jet aeration type mixing systems in which nozzles are positioned along the length of an elongated member. In the example shown in FIG. 11, the elongated member 1102 is positioned along the diameter of the tank 1104, and the nozzles 1106 extend in opposite directions from the nozzle to produce the indicated flow pattern which includes two areas of generally elliptical flow, one on either side of the central elongated member. In the example shown in FIG. 12, the tank 1204 is generally rectangular in cross section, and the elongated member 1202 extends along one side wall 1207 of the tank. In this case, the nozzles 1206 all face in the same direction, towards the opposite side wall 1209. This produces the flow pattern shown, in which flow in the tank is generally elliptical about a major axis extending generally centrally along the length of the tank. In the embodiment shown in FIG. 12, the nozzles may be canted towards the tank floor, e.g., at an angle of from about 15 to 30 degrees from the horizontal.

Figure 13:
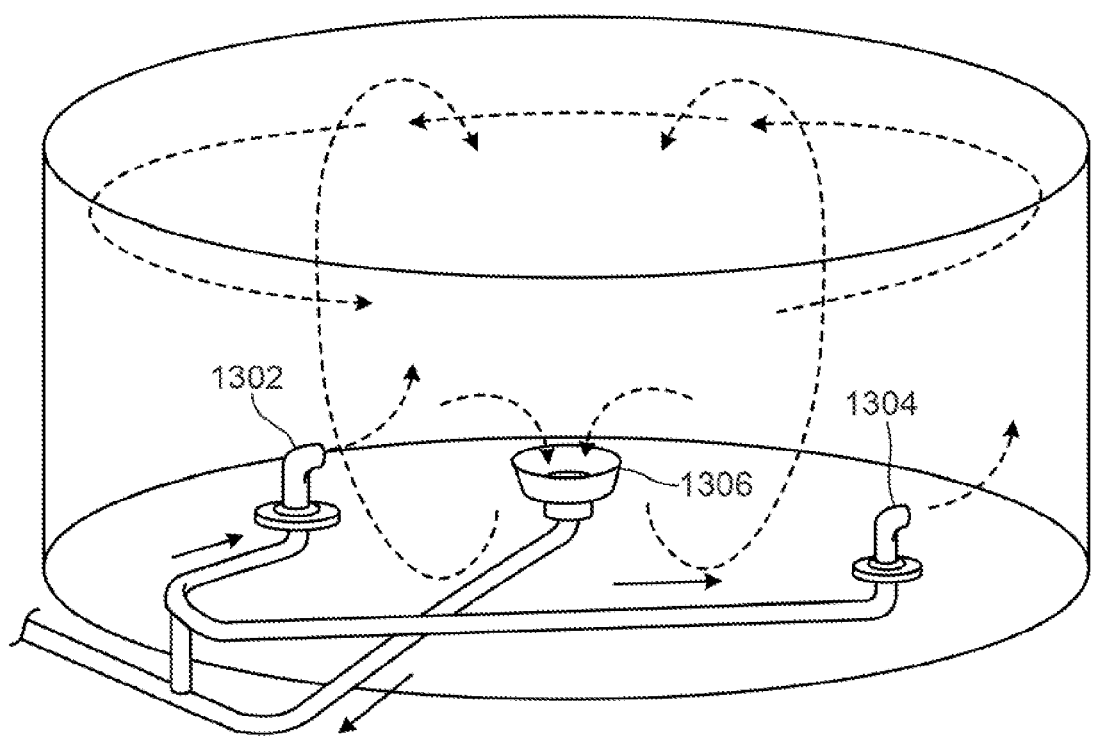

In another embodiment, shown in FIG. 13, the nozzles 1302, 1304, and suction inlet 1306 are arranged to cause the contents of the tank to both revolve and rotate in a toroidal, rolling donut configuration around a central vertical axis of the tank. Flow around the surface of the toroid is drawn down the tank center, along the floor, up the walls and back to the center, creating a rolling helix pattern, which sweeps the center and prevents solids from settling. The toroidal pattern is also effective in moving floating solids to the tank center where they are pulled to the bottom and become homogenous with the tank contents. The result is a continuous helical flow pattern, which minimizes tank dead spots.

Backflushing

Figure 14:
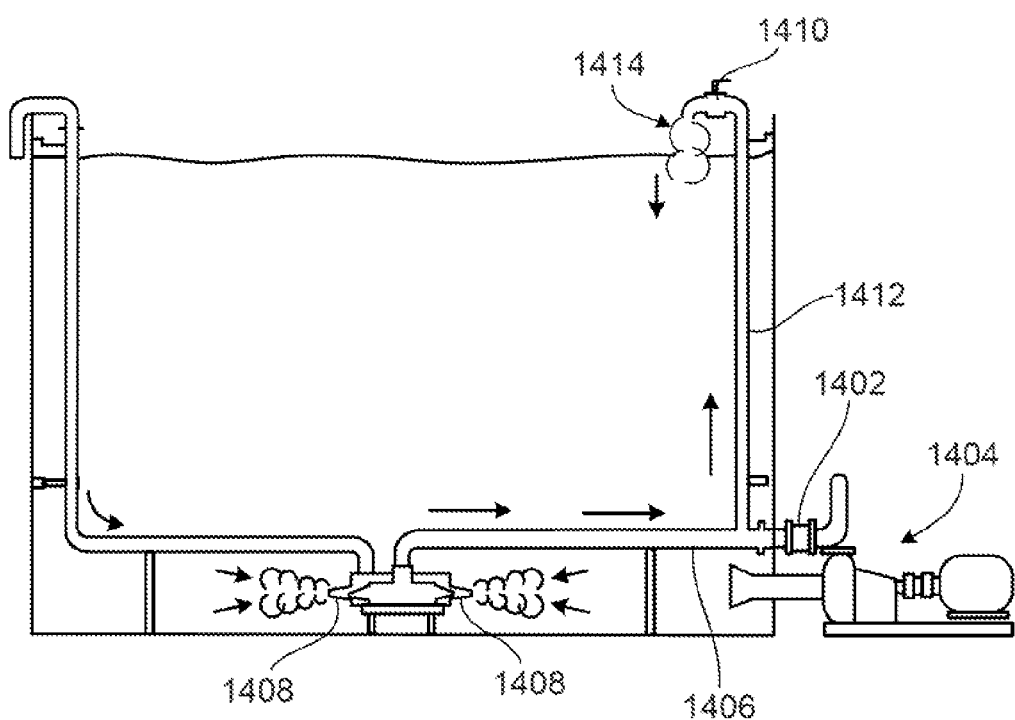
FIG. 14 is a diagram illustrating the flow pattern that occurs in a tank during backflushing according to one embodiment.

In some instances, the jet nozzles described herein can become plugged, which may cause efficiency and cost effectiveness to be reduced. Plugging of the nozzles may be removed by reversing flow of the motive liquid through the nozzle. For example, in the system shown in FIG. 14, this is accomplished by closing a valve 1402 between the pump 1404 and the liquid line 1406 flowing to the nozzles 1408, and activating a secondary pump 1410. Secondary pump 1410 draws fluid in through the nozzles. The fluid then travels up through vertical pipe 1412 due to valve 1402 being closed. The fluid exits the vertical pipe 1412 at its outlet 1414 for recirculation through the tank.

Mixing in Transit/Portable Mixers

Figure 15:
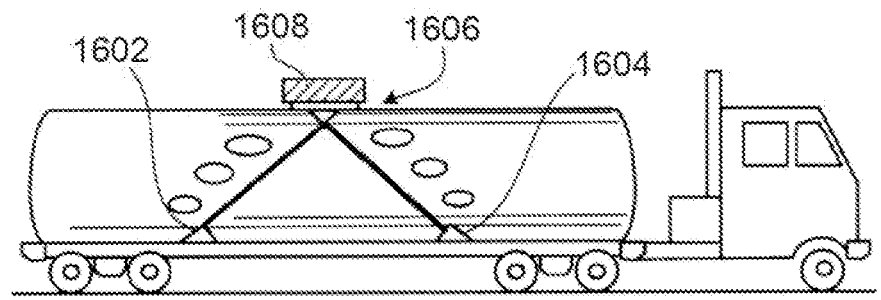
FIGS. 15 and 15A show a tanker truck and a rail car, respectively, set up for in-transit mixing using a pulsed air portable mixing system.
Figure 15A:
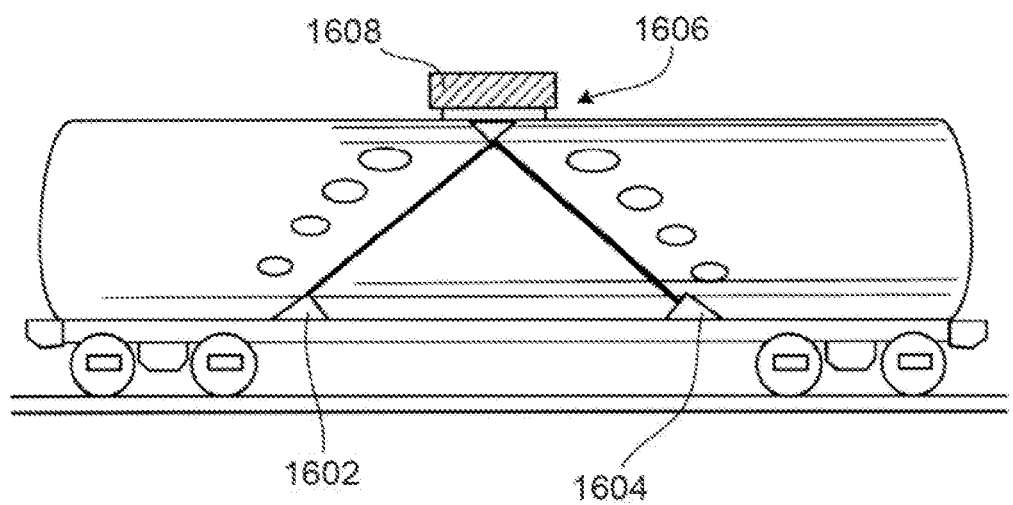

As noted above, if desired saccharification can take place in part or entirely during transportation of the mixture, e.g., between a first processing plant for treating the feedstock and a second processing plant for production of a final product such as ethanol. In this case, mixing can be conducted using a jet mixer designed for rail car or other portable use. Examples of such mixers will be discussed below. As shown diagrammatically in FIGS. 15 and 15A, mixers 1602, 1604 can be inserted through a port 1606 in a tank, e.g., of a truck (FIG. 15) or a railcar (FIG. 15A). The mixer can be operated using a control system 1608 external to the tank, which may include for example a motor and/or a supply or compressed air, depending on the type of mixing system used, and a controller configured to control the operation of the mixer. Venting (not shown) may also be provided.

Other Mixing Systems/Nozzles

Pulsed Air/Fluid

An alternative type of mixer utilizes a gas delivered in pulses to the mixture. Such a mixer is shown diagrammatically in FIGS. 15 and 15A, as an example of a portable railcar mixer. Metered amounts of high pressure gas are injected or pulsed under flat round discs (accumulator plates) positioned near the tank bottom. The sudden release of air shocks the liquid. As the gas moves outward between the plate and the tank floor, it sweeps out solids that have settled. The gas then accumulates above the plate into large, oval shaped bubbles. As each bubble rises to the surface, it pushes the liquid above it up and out towards the tank perimeter. The liquid moves toward the sides of the tank and travels down the tank wall to the bottom. This movement of the bubbles forces solids to the surface and creates a generally circular or toroidal circulation of liquid in the tank. The gas may be, for example, air, nitrogen, or carbon dioxide. The tank is vented (not shown) to allow gas to escape from the tank during mixing.

Low Speed Agitators

Figure 16:
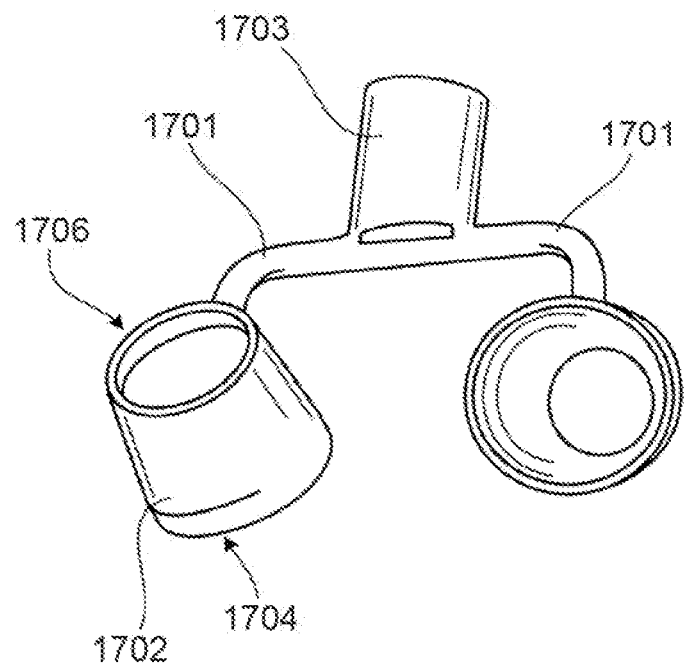
FIGS. 16 and 16A are perspective views of two embodiments of mixing heads used in a mixer according to an alternate embodiment.
Figure 16A:
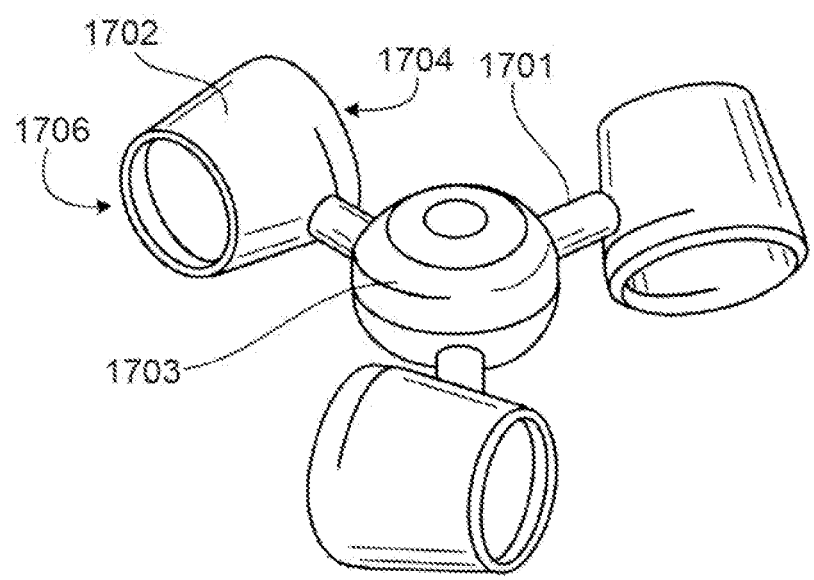
Figure 17:
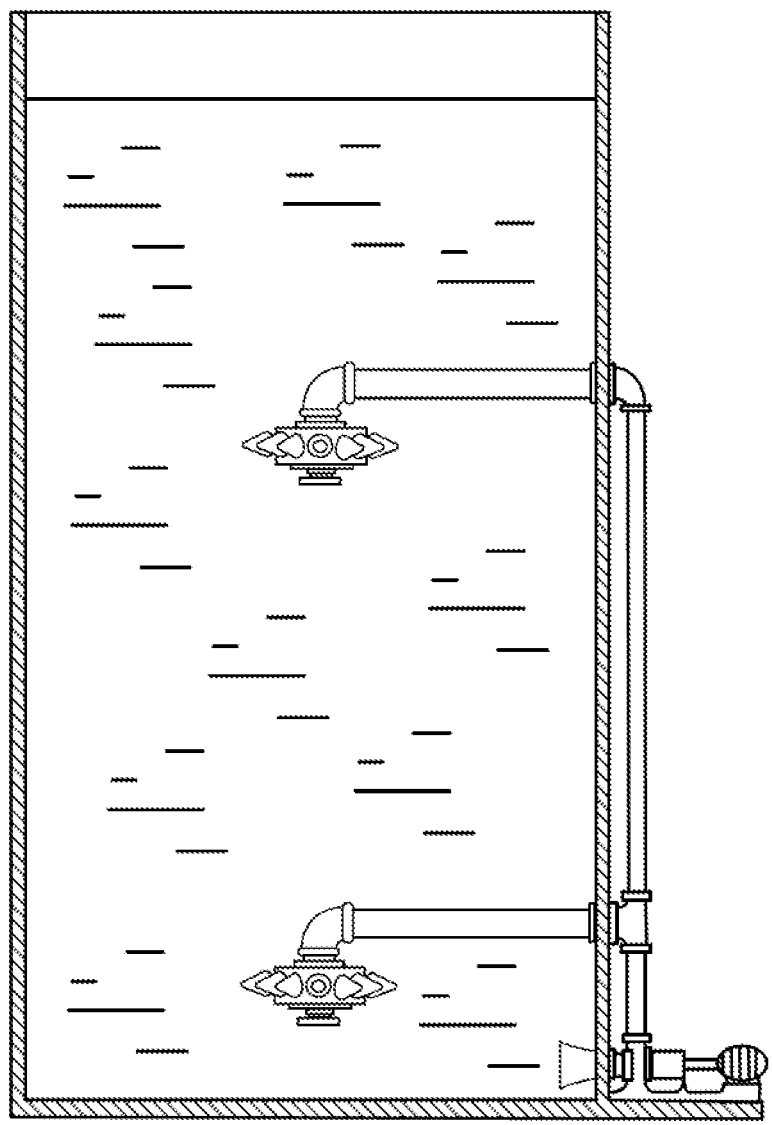
FIG. 17 is a side view of a jet aeration type system according to another embodiment, showing a multi-level arrangement of nozzles in a tank.

FIGS. 16 and 16A illustrate agitators configured to be mounted on a shaft (not shown) for rotational mixing at relatively low speeds. The agitators may include, for example, two mixing elements 1702 (FIG. 16), or three mixing elements (FIG. 16A), mounted on support arms 1701 about a central mounting hub 1703 that is disposed to receive a shaft.

The mixing elements 1702 are in the form of truncated cones, each of which has a first end 1704 and a second end 1706. The first end has a cross-section greater than the cross-section of the second end. The mixing elements are positioned such that the central axes of the mixing elements are disposed at an angle relative to a plane of rotation of the mixing elements.

The agitator is rotated in a direction so that liquid flows in through the first end 1704 and out through the second end 1706 at a higher velocity, creating dynamic flow conditions by generating turbulent flow at the tapered end of each mixing element. The angulation of the mixing elements relative to the plane of rotation tends to cause a continuous closed circular flow which in the vicinity of an adjacent tank or container wall flows upwardly and in the central part of the tank or container flows downwardly coaxially to the mixer shaft where it passes through the intermediate spaces between the support arms 1701. The intensity of this circular flow depends on the magnitude of the angle.

Mixers of this type are available commercially from Inotec under the tradename VISCO-JET™. Folding mixers are available which can be put in rail car or other transport container. A similar type of mixer is described in U.S. Pat. No. 6,921,194, the full disclosure if which is incorporated herein by reference.

Minimizing Hold Up on Tank Walls

In some situations, in particular at solids levels approaching a theoretical or practical limit, material may accumulate along the side wall and/or bottom wall of the tank during mixing. This phenomenon, referred to as "hold up," is undesirable as it can result in inadequate mixing. Several approaches can be taken to minimize hold up and ensure good mixing throughout the tank.

Figure 18:
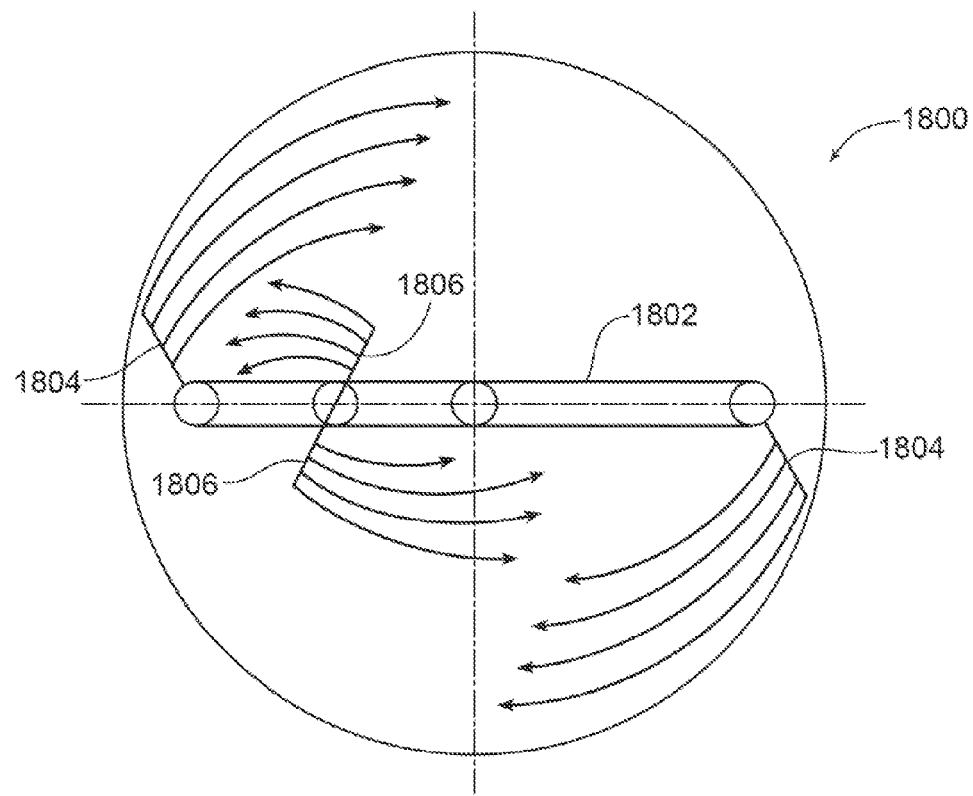
FIGS. 18 and 18A are a diagrammatic top view and a perspective view, respectively, of a device that minimizes hold up along the walls of a tank during mixing.
Figure 18A:
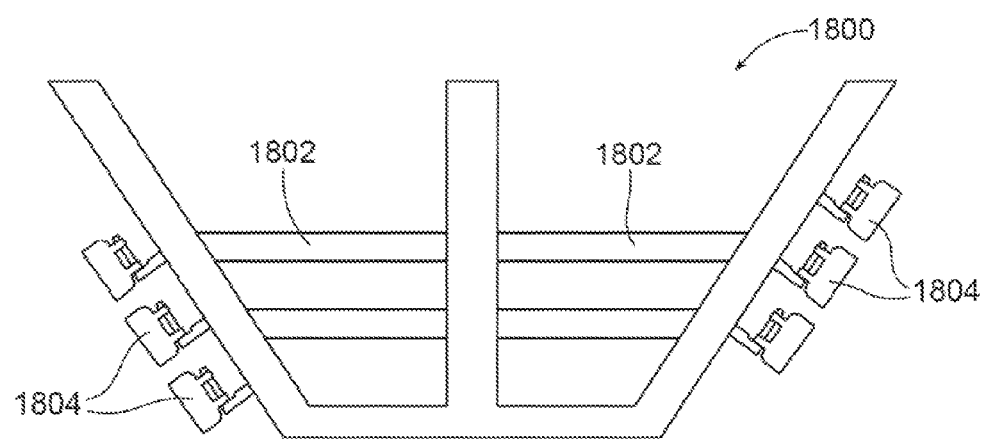

For example, in addition to the jet mixing device(s), the tank can be outfitted with a scraping device, for example a device having a blade that scrapes the side of the tank in a "squeegee" manner. Such devices are well known, for example in the dairy industry. Suitable agitators include the side and bottom sweep agitators and scraper blade agitators manufactured by Walker Engineered Products, New Lisbon, Wis. As shown in FIG. 18, a side and bottom sweep agitator 1800 may include a central elongated member 1802, mounted to rotate about the axis of the tank. Side wall scraper blades 1804 are mounted at each end of the elongated member 1802 and are disposed at an angle with respect to the elongated member. In the embodiment shown, a pair of bottom wall scraper blades 1806 are mounted at an intermediate point on the elongated member 1802, to scrape up any material accumulating on the tank bottom. These scrapers may be omitted if material is not accumulating on the tank bottom. As shown in FIG. 18A, the scraper blades 1804 may be in the form of a plurality of scraper elements positioned along the side wall. In other embodiments, the scraper blades are continuous, or may have any other desired geometry.

In other embodiments, the jet mixer itself is configured so as to minimize hold up. For example, the jet mixer may include one or more movable heads and/or flexible portions that move during mixing. For example, the jet mixer may include an elongated rotatable member having a plurality of jet nozzles along its length. The elongated member may be planar, as shown in FIG. 19, or have a non-planar shape, e.g., it may conform to the shape of the tank walls as shown in FIG. 20.

Referring to FIG. 19, the jet mixer nozzles may be positioned on a rotating elongated member 1900 that is driven by a motor 1902 and shaft 1904. Water or other fluid is pumped through passageways in the rotating member, e.g., by a pump impeller 1906, and exits as a plurality of jets through jet orifices 1908 while the member 1900 rotates. To reduce hold up on the tank side walls, orifices 1910 may be provided at the ends of the member 1900.

In the embodiment shown in FIG. 20, to conform to the particular shape of the tank 2000 the elongated member includes horizontally extending arms 2002, downwardly inclined portions 2004, outwardly and upwardly inclined portions 2006, and vertically extending portions 2008. Fluid is pumped through passageways within the elongated member to a plurality of jet orifices 38, through which jets are emitted while the elongated member is rotated.

In both of the embodiments shown in FIGS. 19 and 20, the jets provide mixing while also washing down the side walls of the tank.

Figure 21:
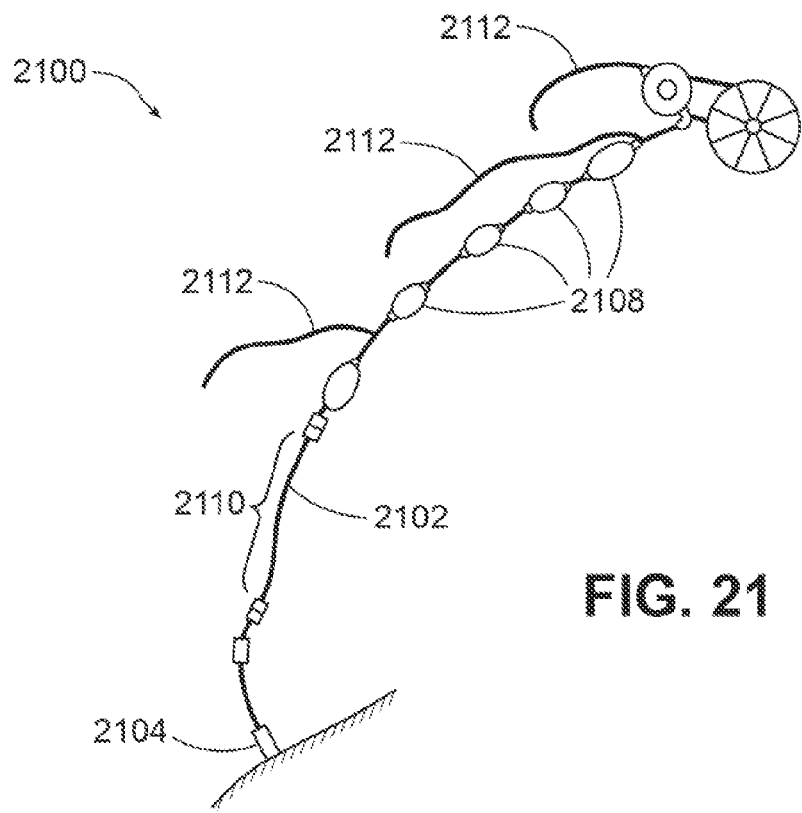
Figure 21A:
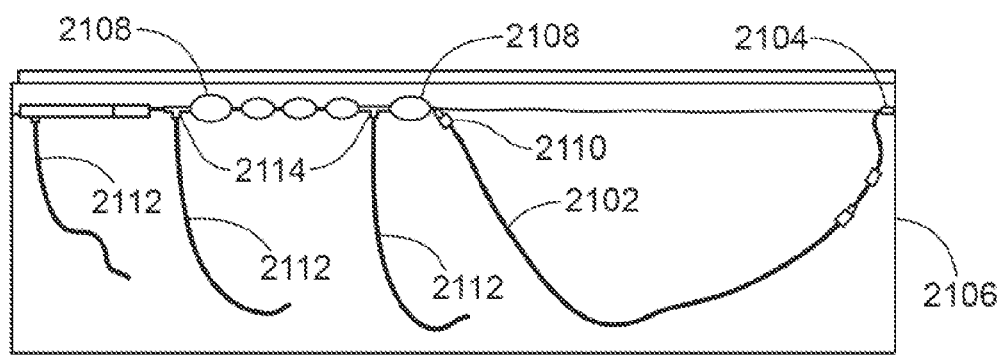

In other embodiments, the jet mixer may include flexible members and or adjustable members (e.g., bendable or telescoping tubes) through which the jets are delivered. For example, as shown diagrammatically in FIGS. 21 and 21A, the jet mixing device may be made up of flexible tubing, in the manner of a floating type of pool cleaner, such as is disclosed in U.S. Pat. No. 3,883,368. In the system 2100 shown, a flexible supply hose 2102 delivers fluid from an inlet 2104 in the sidewall of the tank 2106. The supply hose 2102 extends along the surface of the liquid in the tank via a series of buoys 2108 and swivels 2110. A plurality of flexible hoses 2112 are secured at their upper ends to spaced T-joints 2114 in the floating portion of the supply hose 2102. Fluid is jetted from the open distal ends of the flexible hoses 2112, resulting in mixing of the contents of the tank and removal of hold up on the tank side walls.

In some implementations, combinations of the embodiments described above may be used. For example, combinations of planar and non-planar rotating or oscillating elongated members may be used. The moving nozzle arrangements described above can be used in combination with each other and/or in combination with scrapers. A plurality of moving nozzle arrangements can be used together, for example two or more of the rotating members shown in FIG. 19 can be stacked vertically in the tank. When multiple rotating members are used, they can be configured to rotate in the same direction or in opposite directions, and at the same speed or different speeds.

Physical Treatment

Physical treatment processes can include one or more of any of those described herein, such as mechanical treatment, chemical treatment, irradiation, sonication, oxidation, pyrolysis or steam explosion. Treatment methods can be used in combinations of two, three, four, or even all of these technologies (in any order). When more than one treatment method is used, the methods can be applied at the same time or at different times. Other processes that change a molecular structure of a feedstock may also be used, alone or in combination with the processes disclosed herein.

Mechanical Treatments

In some cases, methods can include mechanically treating the feedstock. Mechanical treatments include, for example, cutting, milling, pressing, grinding, shearing and chopping. Milling may include, for example, ball milling, hammer milling, rotor/stator dry or wet milling, freezer milling, blade milling, knife milling, disk milling, roller milling or other types of milling. Other mechanical treatments include, e.g., stone grinding, cracking, mechanical ripping or tearing, pin grinding or air attrition milling.

Mechanical treatment can be advantageous for "opening up," "stressing," breaking and shattering cellulosic or other materials in the feedstock, making the cellulose of the materials more susceptible to chain scission and/or reduction of crystallinity. The open materials can also be more susceptible to oxidation when irradiated.

In some cases, the mechanical treatment may include an initial preparation of the feedstock as received, e.g., size reduction of materials, such as by cutting, grinding, shearing, pulverizing or chopping. For example, in some cases, loose feedstock (e.g., Machine Offset Paper and/or Poly-coated Paper) is prepared by shearing or shredding.

Alternatively, or in addition, the feedstock material can first be physically treated by one or more of the other physical treatment methods, e.g., chemical treatment, radiation, sonication, oxidation, pyrolysis or steam explosion, and then mechanically treated. This sequence can be advantageous since materials treated by one or more of the other treatments, e.g., irradiation or pyrolysis, tend to be more brittle and, therefore, it may be easier to further change the molecular structure of the material by mechanical treatment.

In some embodiments, mechanical treatment includes shearing to expose fibers of the material. Shearing can be performed, for example, using a rotary knife cutter. Other methods of mechanically treating the feedstock include, for example, milling or grinding. Milling may be performed using, for example, a hammer mill, ball mill, colloid mill, conical or cone mill, disk mill, edge mill, Wiley mill or grist mill. Grinding may be performed using, for example, a stone grinder, pin grinder, coffee grinder, or burr grinder. Grinding may be provided, for example, by a reciprocating pin or other element, as is the case in a pin mill. Other mechanical treatment methods include mechanical ripping or tearing, other methods that apply pressure to the material, and air attrition milling. Suitable mechanical treatments further include any other technique that changes the molecular structure of the feedstock.

If desired, the mechanically treated material can be passed through a screen, e.g., having an average opening size of 1.59 mm or less (1/16 inch, 0.0625 inch). In some embodiments, shearing, or other mechanical treatment, and screening are performed concurrently. For example, a rotary knife cutter can be used to concurrently shear and screen the feedstock. The feedstock is sheared between stationary blades and rotating blades to provide a sheared material that passes through a screen, and is captured in a bin.

The paper feedstock can be mechanically treated in a dry state (e.g., having little or no free water on its surface), a hydrated state (e.g., having up to ten percent by weight absorbed water), or in a wet state, e.g., having between about 10 percent and about 75 percent by weight water. The fiber source can even be mechanically treated while partially or fully submerged under a liquid, such as water, ethanol or isopropanol.

The feedstock can also be mechanically treated under a gas (such as a stream or atmosphere of gas other than air), e.g., oxygen or nitrogen, or steam.

Mechanical treatment systems can be configured to produce streams with specific morphology characteristics such as, for example, surface area, porosity, bulk density, and length-to-width ratio.

In some embodiments, a BET surface area of the mechanically treated material is greater than 0.1 m$^2$/g, e.g., greater than 0.25 m$^2$/g, greater than 0.5 m$^2$/g, greater than 1.0 m$^2$/g, greater than 1.5 m$^2$/g, greater than 1.75 m$^2$/g, greater than 5.0 m$^2$/g, greater than 10 m$^2$/g, greater than 25 m$^2$/g, greater than 35 m$^2$/g, greater than 50 m$^2$/g, greater than 60 m$^2$/g, greater than 75 m$^2$/g, greater than 100 m$^2$/g, greater than 150 m$^2$/g, greater than 200 m$^2$/g, or even greater than 250 m$^2$/g.

In some situations, it can be desirable to prepare a low bulk density material, densify the material (e.g., to make it easier and less costly to transport to another site), and then revert the material to a lower bulk density state. Densified materials can be processed by any of the methods described herein, or any material processed by any of the methods described herein can be subsequently densified, e.g., as disclosed in U.S. Ser. No. 12/429,045, filed Apr. 23, 2009, now U.S. Pat. No. 7,932,065, and WO 2008/073186, the full disclosures of which are incorporated herein by reference.

Radiation Treatment

One or more radiation processing sequences can be used to process the paper feedstock, and to provide a structurally modified material which functions as input to further processing steps and/or sequences. Irradiation can, for example, reduce the molecular weight and/or crystallinity of feedstock. Radiation can also sterilize the materials, or any media needed to bioprocess the material.

In some embodiments, the radiation may be provided by (1) heavy charged particles, such as alpha particles or protons, (2) electrons, produced, for example, in beta decay or electron beam accelerators, or (3) electromagnetic radiation, for example, gamma rays, x rays, or ultraviolet rays. In one approach, radiation produced by radioactive substances can be used to irradiate the feedstock. In another approach, electromagnetic radiation (e.g., produced using electron beam emitters) can be used to irradiate the feedstock. In some embodiments, any combination in any order or concurrently of (1) through (3) may be utilized. The doses applied depend on the desired effect and the particular feedstock.

In some instances when chain scission is desirable and/or polymer chain functionalization is desirable, particles heavier than electrons, such as protons, helium nuclei, argon ions, silicon ions, neon ions, carbon ions, phosphorus ions, oxygen ions or nitrogen ions can be utilized. When ring-opening chain scission is desired, positively charged particles can be utilized for their Lewis acid properties for enhanced ring-opening chain scission. For example, when maximum oxidation is desired, oxygen ions can be utilized, and when maximum nitration is desired, nitrogen ions can be utilized. The use of heavy particles and positively charged particles is described in U.S. Ser. No. 12/417,699, filed Apr. 3, 2009, now U.S. Pat. No. 7,931,784, the full disclosure of which is incorporated herein by reference.

In one method, a first material that is or includes cellulose having a first number average molecular weight ($M_{N1}$) is irradiated, e.g., by treatment with ionizing radiation (e.g., in the form of gamma radiation, X-ray radiation, 100 nm to 280 nm ultraviolet (UV) light, a beam of electrons or other charged particles) to provide a second material that includes cellulose having a second number average molecular weight ($M_{N2}$) lower than the first number average molecular weight. The second material (or the first and second material) can be combined with a microorganism (with or without enzyme treatment) that can utilize the second and/or first material or its constituent sugars or lignin to produce an intermediate or product, such as those described herein.

Since the second material includes cellulose having a reduced molecular weight relative to the first material, and in some instances, a reduced crystallinity as well, the second material is generally more dispersible, swellable and/or soluble, e.g., in a solution containing a microorganism and/or an enzyme. These properties make the second material easier to process and more susceptible to chemical, enzymatic and/or biological attack relative to the first material, which can greatly improve the production rate and/or production level of a desired product, e.g., ethanol.

In some embodiments, the second number average molecular weight ($M_{N2}$) is lower than the first number average molecular weight ($M_{N1}$) by more than about 10 percent, e.g., more than about 15, 20, 25, 30, 35, 40, 50 percent, 60 percent, or even more than about 75 percent.

In some instances, the second material includes cellulose that has a crystallinity ($C_2$) that is lower than the crystallinity ($C_1$) of the cellulose of the first material. For example, ($C_2$) can be lower than ($C_1$) by more than about 10 percent, e.g., more than about 15, 20, 25, 30, 35, 40, or even more than about 50 percent.

In some embodiments, the second material can have a level of oxidation ($O_2$) that is higher than the level of oxidation ($O_1$) of the first material. A higher level of oxidation of the material can aid in its dispersability, swellability and/or solubility, further enhancing the material's susceptibility to chemical, enzymatic or biological attack. In some embodiments, to increase the level of the oxidation of the second material relative to the first material, the irradiation is performed under an oxidizing environment, e.g., under a blanket of air or oxygen, producing a second material that is more oxidized than the first material. For example, the second material can have more hydroxyl groups, aldehyde groups, ketone groups, ester groups or carboxylic acid groups, which can increase its hydrophilicity.

Ionizing Radiation

Each form of radiation ionizes the paper feedstock via particular interactions, as determined by the energy of the radiation. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired, positively charged particles may be desirable, in part due to their acidic nature. When particles are utilized, the particles can have the mass of a resting electron, or greater, e.g., 500, 1000, 1500, 2000, 10,000 or even 100,000 times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 amu. Accelerators used to accelerate the particles can be electrostatic DC, electrodynamic DC, RF linear, magnetic induction linear or continuous wave. For example, cyclotron type accelerators are available from IBA, Belgium, such as the RHODO-TRON® system, while DC type accelerators are available from RDI, now IBA Industrial, such as the DYNA-MITRON®. Ions and ion accelerators are discussed in Introductory Nuclear Physics, Kenneth S. Krane, John Wiley & Sons, Inc. (1988), Krsto Prelec, FIZIKA B 6 (1997) 4, 177-206, Chu, William T., "Overview of Light-Ion Beam Therapy" Columbus-Ohio, ICRU-IAEA Meeting, 18-20 Mar. 2006, Iwata, Y. et al., "Alternating-Phase-Focused IH-DTL for Heavy-Ion Medical Accelerators" Proceedings of EPAC 2006, Edinburgh, Scotland and Leaner, C. M. et al., "Status of the Superconducting ECR Ion Source Venus" Proceedings of EPAC 2000, Vienna, Austria.

Gamma radiation has the advantage of a significant penetration depth into a variety of materials. Sources of gamma rays include radioactive nuclei, such as isotopes of cobalt, calcium, technicium, chromium, gallium, indium, iodine, iron, krypton, samarium, selenium, sodium, thalium, and xenon.

Sources of x rays include electron beam collision with metal targets, such as tungsten or molybdenum or alloys, or compact light sources, such as those produced commercially by Lyncean.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

In some embodiments, a beam of electrons is used as the radiation source. A beam of electrons has the advantages of high dose rates (e.g., 1, 5, or even 10 Mrad per second), high throughput, less containment, and less confinement equipment. Electrons can also be more efficient at causing chain scission. In addition, electrons having energies of 4-10 MeV can have a penetration depth of 5 to 30 mm or more, such as 40 mm.

Electron beams can be generated, e.g., by electrostatic generators, cascade generators, transformer generators, low energy accelerators with a scanning system, low energy accelerators with a linear cathode, linear accelerators, and pulsed accelerators. Electrons as an ionizing radiation source can be useful, e.g., for relatively thin sections of material, e.g., less than 0.5 inch, e.g., less than 0.4 inch, 0.3 inch, 0.2 inch, or less than 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV.

Electron beam irradiation devices may be procured commercially from Ion Beam Applications, Louvain-la-Neuve, Belgium or the Titan Corporation, San Diego, Calif. Typical electron energies can be 1 MeV, 2 MeV, 4.5 MeV, 7.5 MeV, or 10 MeV. Typical electron beam irradiation device power can be 1 kW, 5 kW, 10 kW, 20 kW, 50 kW, 100 kW, 250 kW, or 500 kW. The level of depolymerization of the feedstock depends on the electron energy used and the dose applied, while exposure time depends on the power and dose. Typical doses may take values of 1 kGy, 5 kGy, 10 kGy, 20 kGy, 50 kGy, 100 kGy, or 200 kGy. In a some embodiments energies between 0.25-10 MeV (e.g., 0.5-0.8 MeV, 0.5-5 MeV, 0.8-4 MeV, 0.8-3 MeV, 0.8-2 MeV or 0.8-1.5 MeV) can be used. In some embodiment doses between 1-100 Mrad (e.g., 2-80 Mrad, 5-50 Mrad, 5-40 Mrad, 5-30 Mrad or 5-20 Mrad) can be used. In some preferred embodiments, an energy between 0.8-3 MeV (e.g., 0.8-2 MeV or 0.8-1.5 MeV) combined with doses between 5-50 Mrad (e.g., 5-40 Mrad, 5-30 Mrad or 5-20 Mrad) can be used.

Ion Particle Beams

Particles heavier than electrons can be utilized to irradiate paper feedstock materials. For example, protons, helium nuclei, argon ions, silicon ions, neon ions carbon ions, phosphorus ions, oxygen ions or nitrogen ions can be utilized. In some embodiments, particles heavier than electrons can induce higher amounts of chain scission (relative to lighter particles). In some instances, positively charged particles can induce higher amounts of chain scission than negatively charged particles due to their acidity.

Heavier particle beams can be generated, e.g., using linear accelerators or cyclotrons. In some embodiments, the energy of each particle of the beam is from about 1.0 MeV/atomic unit (MeV/amu) to about 6,000 MeV/atomic unit, e.g., from about 3 MeV/atomic unit to about 4,800 MeV/atomic unit, or from about 10 MeV/atomic unit to about 1,000 MeV/atomic unit.

In certain embodiments, ion beams used to irradiate paper feedstock can include more than one type of ion. For example, ion beams can include mixtures of two or more (e.g., three, four or more) different types of ions. Exemplary mixtures can include carbon ions and protons, carbon ions and oxygen ions, nitrogen ions and protons, and iron ions and protons. More generally, mixtures of any of the ions discussed above (or any other ions) can be used to form irradiating ion beams. In particular, mixtures of relatively light and relatively heavier ions can be used in a single ion beam.

In some embodiments, ion beams for irradiating paper feedstock include positively-charged ions. The positively charged ions can include, for example, positively charged hydrogen ions (e.g., protons), noble gas ions (e.g., helium, neon, argon), carbon ions, nitrogen ions, oxygen ions, silicon atoms, phosphorus ions, and metal ions such as sodium ions, calcium ions, and/or iron ions. Without wishing to be bound by any theory, it is believed that such positively-charged ions behave chemically as Lewis acid moieties when exposed to materials, initiating and sustaining cationic ring-opening chain scission reactions in an oxidative environment.

In certain embodiments, ion beams for irradiating paper feedstock include negatively-charged ions. Negatively charged ions can include, for example, negatively charged hydrogen ions (e.g., hydride ions), and negatively charged ions of various relatively electronegative nuclei (e.g., oxygen ions, nitrogen ions, carbon ions, silicon ions, and phosphorus ions). Without wishing to be bound by any theory, it is believed that such negatively-charged ions behave chemically as Lewis base moieties when exposed to materials, causing anionic ring-opening chain scission reactions in a reducing environment.

In some embodiments, beams for irradiating paper feedstock can include neutral atoms. For example, any one or more of hydrogen atoms, helium atoms, carbon atoms, nitrogen atoms, oxygen atoms, neon atoms, silicon atoms, phosphorus atoms, argon atoms, and iron atoms can be included in beams that are used for irradiation. In general, mixtures of any two or more of the above types of atoms (e.g., three or more, four or more, or even more) can be present in the beams.

In certain embodiments, ion beams used to irradiate paper feedstock include singly-charged ions such as one or more of $H^+$, $H^-$, $He^+$, $Ne^+$, $Ar^+$, $C^+$, $C^-$, $O^+$, $O^-$, $N^+$, $N^-$, $Si^+$, $Si^-$, $P^+$, $P^-$, $Na^+$, $Ca^+$ and $Fe^+$. In some embodiments, ion beams can include multiply-charged ions such as one or more of $C^{2+}$, $C^{3+}$, $C^{4+}$, $N^{3+}$, $N^{5+}$, $N^{3-}$, $O^{2+}$, $O^{2-}$, $O_2^{2-}$, $Si^{2+}$, $Si^{4+}$, $Si^{2-}$, and $Si^{4-}$. In general, the ion beams can also include more complex polynuclear ions that bear multiple positive or negative charges. In certain embodiments, by virtue of the structure of the polynuclear ion, the positive or negative charges can be effectively distributed over substantially the entire structure of the ions. In some embodiments, the positive or negative charges can be somewhat localized over portions of the structure of the ions.

Electromagnetic Radiation

In embodiments in which the irradiating is performed with electromagnetic radiation, the electromagnetic radiation can have, e.g., energy per photon (in electron volts) of greater than $10^2$ eV, e.g., greater than $10^3$, $10^4$, $10^5$, $10^6$, or even greater than $10^7$ eV. In some embodiments, the electromagnetic radiation has energy per photon of between $10^4$ and $10^7$, e.g., between $10^5$ and $10^6$ eV. The electromagnetic radiation can have a frequency of, e.g., greater than $10^{16}$ hz, than $10^{17}$ hz, $10^{18}$, $10^{19}$, $10^{20}$, or even greater than $10^{21}$ hz. Typical doses may take values of greater than 1 Mrad (e.g., greater than 1 Mrad, greater than 2 Mrad). In some embodiments, the electromagnetic radiation has a frequency of between $10^{18}$ and $10^{22}$ hz, e.g., between $10^{19}$ to $10^{21}$ hz. In some embodiment doses between 1-100 Mrad (e.g., 2-80 Mrad, 5-50 Mrad, 5-40 Mrad, 5-30 Mrad or 5-20 Mrad) can be used.

Quenching and Controlled Functionalization

After treatment with ionizing radiation, any of the materials or mixtures described herein may become ionized; that is, the treated material may include radicals at levels that are detectable with an electron spin resonance spectrometer. If an ionized feedstock remains in the atmosphere, it will be oxidized, such as to an extent that carboxylic acid groups are generated by reacting with the atmospheric oxygen. In some instances with some materials, such oxidation is desired because it can aid in the further breakdown in molecular weight of the carbohydrate-containing biomass, and the oxidation groups, e.g., carboxylic acid groups can be helpful for solubility and microorganism utilization in some instances. However, since the radicals can "live" for some time after irradiation, e.g., longer than 1 day, 5 days, 30 days, 3 months, 6 months or even longer than 1 year, material properties can continue to change over time, which in some instances, can be undesirable. Thus, it may be desirable to quench the ionized material.

After ionization, any ionized material can be quenched to reduce the level of radicals in the ionized material, e.g., such that the radicals are no longer detectable with the electron spin resonance spectrometer. For example, the radicals can be quenched by the application of a sufficient pressure to the material and/or by utilizing a fluid in contact with the ionized material, such as a gas or liquid, that reacts with (quenches) the radicals. Using a gas or liquid to at least aid in the quenching of the radicals can be used to functionalize the ionized material with a desired amount and kind of functional groups, such as carboxylic acid groups, enol groups, aldehyde groups, nitro groups, nitrile groups, amino groups, alkyl amino groups, alkyl groups, chloroalkyl groups or chlorofluoroalkyl groups.

In some instances, such quenching can improve the stability of some of the ionized materials. For example, quenching can improve the resistance of the material to oxidation. Functionalization by quenching can also improve the solubility of any material described herein, can improve its thermal stability, and can improve material utilization by various microorganisms. For example, the functional groups imparted to the material by the quenching can act as receptor sites for attachment by microorganisms, e.g., to enhance cellulose hydrolysis by various microorganisms.

In some embodiments, quenching includes an application of pressure to the ionized material, such as by mechanically deforming the material, e.g., directly mechanically compressing the material in one, two, or three dimensions, or applying pressure to a fluid in which the material is immersed, e.g., isostatic pressing. In such instances, the deformation of the material itself brings radicals, which are often trapped in crystalline domains, in close enough proximity so that the radicals can recombine, or react with another group. In some instances, the pressure is applied together with the application of heat, such as a sufficient quantity of heat to elevate the temperature of the material to above a melting point or softening point of a component of the material, such cellulose or another polymer. Heat can improve molecular mobility in the material, which can aid in the quenching of the radicals. When pressure is utilized to quench, the pressure can be greater than about 1000 psi, such as greater than about 1250 psi, 1450 psi, 3625 psi, 5075 psi, 7250 psi, 10000 psi or even greater than 15000 psi.

In some embodiments, quenching includes contacting the ionized material with a fluid, such as a liquid or gas, e.g., a gas capable of reacting with the radicals, such as acetylene or a mixture of acetylene in nitrogen, ethylene, chlorinated ethylenes or chlorofluoroethylenes, propylene or mixtures of these gases. In other particular embodiments, quenching includes contacting the ionized material with a liquid, e.g., a liquid soluble in, or at least capable of penetrating into the material and reacting with the radicals, such as a diene, such as 1,5-cyclooctadiene. In some specific embodiments, quenching includes contacting the material with an antioxidant, such as Vitamin E. If desired, the feedstock can include an antioxidant dispersed therein, and the quenching can come from contacting the antioxidant dispersed in the feedstock with the radicals.

Functionalization can be enhanced by utilizing heavy charged ions, such as any of the heavier ions described herein. For example, if it is desired to enhance oxidation, charged oxygen ions can be utilized for the irradiation. If nitrogen functional groups are desired, nitrogen ions or anions that include nitrogen can be utilized. Likewise, if sulfur or phosphorus groups are desired, sulfur or phosphorus ions can be used in the irradiation.

Doses

In some instances, the irradiation is performed at a dosage rate of greater than about 0.25 Mrad per second, e.g., greater than about 0.5, 0.75, 1.0, 1.5, 2.0, or even greater than about 2.5 Mrad per second. In some embodiments, the irradiating is performed at a dose rate of between 5.0 and 1500.0 kilorads/hour, e.g., between 10.0 and 750.0 kilorads/hour or between 50.0 and 350.0 kilorads/hour. In some embodiments, irradiation is performed at a dose rate of greater than about 0.25 Mrad per second, e.g., greater than about 0.5, 0.75, 1, 1.5, 2, 5, 7, 10, 12, 15, or even greater than about 20 Mrad per second, e.g., about 0.25 to 2 Mrad per second.

In some embodiments, the irradiating (with any radiation source or a combination of sources) is performed until the material receives a dose of 0.25 Mrad, e.g., at least 1.0, 2.5, 5.0, 8.0, 10, 15, 20, 25, 30, 35, 40, 50, or even at least 100 Mrad. In some embodiments, the irradiating is performed until the material receives a dose of between 1.0 Mrad and 6.0 Mrad, e.g., between 1.5 Mrad and 4.0 Mrad, 2 Mrad and 10 Mrad, 5 Mrad and 20 Mrad, 10 Mrad and 30 Mrad, 10 Mrad and 40 Mrad, or 20 Mrad and 50 Mrad. In some embodiments, the irradiating is performed until the material receives a dose of from about 0.1 Mrad to about 500 Mrad, from about 0.5 Mrad to about 200 Mrad, from about 1 Mrad to about 100 Mrad, or from about 5 Mrad to about 60 Mrad. In some embodiments, a relatively low dose of radiation is applied, e.g., less than 60 Mrad.

Sonication

Sonication can reduce the molecular weight and/or crystallinity of the polymers comprising the paper feedstock, e.g., cellulose. Sonication can also be used to sterilize the materials. As discussed above with regard to radiation, the process parameters used for sonication can be varied depending on various factors.

In one method, a first material that includes cellulose having a first number average molecular weight ($M_{N1}$) is dispersed in a medium, such as water, and sonicated and/or otherwise cavitated, to provide a second material that includes cellulose having a second number average molecular weight ($M_{N2}$) lower than the first number average molecular weight. The second material (or the first and second material in certain embodiments) can be combined with a microorganism (with or without enzyme treatment) that can utilize the second and/or first material to produce an intermediate or product.

Since the second material includes cellulose having a reduced molecular weight relative to the first material, and in some instances, a reduced crystallinity as well, the second material is generally more dispersible, swellable, and/or soluble, e.g., in a solution containing a microorganism.

In some embodiments, the second number average molecular weight ($M_{N2}$) is lower than the first number average molecular weight ($M_{N1}$) by more than about 10 percent, e.g., more than about 15, 20, 25, 30, 35, 40, 50 percent, 60 percent, or even more than about 75 percent.

In some instances, the second material includes cellulose that has a crystallinity ($C_2$) that is lower than the crystallinity ($C_1$) of the cellulose of the first material. For example, ($C_2$) can be lower than ($C_1$) by more than about 10 percent, e.g., more than about 15, 20, 25, 30, 35, 40, or even more than about 50 percent.

In some embodiments, the sonication medium is an aqueous medium. If desired, the medium can include an oxidant, such as a peroxide (e.g., hydrogen peroxide), a dispersing agent and/or a buffer. Examples of dispersing agents include ionic dispersing agents, e.g., sodium lauryl sulfate, and non-ionic dispersing agents, e.g., poly(ethylene glycol).

In other embodiments, the sonication medium is non-aqueous. For example, the sonication can be performed in a hydrocarbon, e.g., toluene or heptane, an ether, e.g., diethyl ether or tetrahydrofuran, or even in a liquefied gas such as argon, xenon, or nitrogen.

Pyrolysis

One or more pyrolysis processing sequences can be used to process paper feedstock from a wide variety of different sources to extract useful substances from the materials, and to provide partially degraded materials which function as input to further processing steps and/or sequences. Pyrolysis can also be used to sterilize the materials. Pyrolysis conditions can be varied depending on the characteristics of the feedstock and/or other factors.

In one example, a first material that includes cellulose having a first number average molecular weight ($M_{N1}$) is pyrolyzed, e.g., by heating the first material in a tube furnace (in the presence or absence of oxygen), to provide a second material that includes cellulose having a second number average molecular weight ($M_{N2}$) lower than the first number average molecular weight.

Since the second material includes cellulose having a reduced molecular weight relative to the first material, and in some instances, a reduced crystallinity as well, the second material is generally more dispersible, swellable and/or soluble, e.g., in a solution containing a microorganism.

In some embodiments, the second number average molecular weight ($M_{N2}$) is lower than the first number average molecular weight ($M_{N1}$) by more than about 10 percent, e.g., more than about 15, 20, 25, 30, 35, 40, 50 percent, 60 percent, or even more than about 75 percent.

In some instances, the second material includes cellulose that has a crystallinity ($C_2$) that is lower than the crystallinity ($C_1$) of the cellulose of the first material. For example, ($C_2$) can be lower than ($C_1$) by more than about 10 percent, e.g., more than about 15, 20, 25, 30, 35, 40, or even more than about 50 percent.

In some embodiments, the pyrolysis of the materials is continuous. In other embodiments, the material is pyrolyzed for a pre-determined time, and then allowed to cool for a second pre-determined time before pyrolyzing again.

Oxidation

One or more oxidative processing sequences can be used to process paper feedstock from a wide variety of different sources to extract useful substances from the feedstock, and to provide partially degraded and/or altered feedstock which functions as input to further processing steps and/or sequences. The oxidation conditions can be varied, e.g., depending on the lignin content of the feedstock, with a higher degree of oxidation generally being desired for higher lignin content feedstocks.

In one method, a first material that includes cellulose having a first number average molecular weight ($M_{N1}$) and having a first oxygen content ($O_1$) is oxidized, e.g., by heating the first material in a stream of air or oxygen-enriched air, to provide a second material that includes cellulose having a second number average molecular weight ($M_{N2}$) and having a second oxygen content ($O_2$) higher than the first oxygen content ($O_1$).

The second number average molecular weight of the second material is generally lower than the first number average molecular weight of the first material. For example, the molecular weight may be reduced to the same extent as discussed above with respect to the other physical treatments. The crystallinity of the second material may also be reduced to the same extent as discussed above with respect to the other physical treatments.

In some embodiments, the second oxygen content is at least about five percent higher than the first oxygen content, e.g., 7.5 percent higher, 10.0 percent higher, 12.5 percent higher, 15.0 percent higher or 17.5 percent higher. In some preferred embodiments, the second oxygen content is at least about 20.0 percent higher than the first oxygen content of the first material. Oxygen content is measured by elemental analysis by pyrolyzing a sample in a furnace operating at 1300° C. or higher. A suitable elemental analyzer is the LECO CHNS-932 analyzer with a VTF-900 high temperature pyrolysis furnace.

Generally, oxidation of a material occurs in an oxidizing environment. For example, the oxidation can be effected or aided by pyrolysis in an oxidizing environment, such as in air or argon enriched in air. To aid in the oxidation, various chemical agents, such as oxidants, acids or bases can be added to the material prior to or during oxidation. For example, a peroxide (e.g., benzoyl peroxide) can be added prior to oxidation.

Some oxidative methods of reducing recalcitrance in a paper feedstock employ Fenton-type chemistry. Such methods are disclosed, for example, in U.S. Ser. No. 12/639,289, filed Dec. 16, 2009, now U.S. Pat. No. 8,951,778, the complete disclosure of which is incorporated herein by reference.

Exemplary oxidants include peroxides, such as hydrogen peroxide and benzoyl peroxide, persulfates, such as ammonium persulfate, activated forms of oxygen, such as ozone, permanganates, such as potassium permanganate, perchlorates, such as sodium perchlorate, and hypochlorites, such as sodium hypochlorite (household bleach).

In some situations, pH is maintained at or below about 5.5 during contact, such as between 1 and 5, between 2 and 5, between 2.5 and 5 or between about 3 and 5. Oxidation conditions can also include a contact period of between 2 and 12 hours, e.g., between 4 and 10 hours or between 5 and 8 hours. In some instances, temperature is maintained at or below 300° C., e.g., at or below 250, 200, 150, 100 or 50° C. In some instances, the temperature remains substantially ambient, e.g., at or about 20-25° C.

In some embodiments, the one or more oxidants are applied as a gas, such as by generating ozone in-situ by irradiating the material through air with a beam of particles, such as electrons.

In some embodiments, the mixture further includes one or more hydroquinones, such as 2,5-dimethoxyhydroquinone (DMHQ) and/or one or more benzoquinones, such as 2,5-dimethoxy-1,4-benzoquinone (DMBQ), which can aid in electron transfer reactions.

In some embodiments, the one or more oxidants are electrochemically-generated in-situ. For example, hydrogen peroxide and/or ozone can be electro-chemically produced within a contact or reaction vessel.

Other Processes to Solubilize, Reduce Recalcitrance or to Functionalize

Any of the processes of this paragraph can be used alone without any of the processes described herein, or in combination with any of the processes described herein (in any order): steam explosion, chemical treatment (e.g., acid treatment (including concentrated and dilute acid treatment with mineral acids, such as sulfuric acid, hydrochloric acid and organic acids, such as trifluoroacetic acid) and/or base treatment (e.g., treatment with lime or sodium hydroxide)), UV treatment, screw extrusion treatment (see, e.g., U.S. Ser. No. 13/099,151, filed May 2, 2011, now U.S. Pat. No. 8,945,352, solvent treatment (e.g., treatment with ionic liquids) and freeze milling (see, e.g., U.S. Ser. No. 12/502, 629, filed Jul. 14, 2009, now U.S. Pat. No. 7,900,857).

Saccharification

In order to convert the paper feedstock to fermentable sugars, the cellulose in the feedstock is hydrolyzed by a saccharifying agent, e.g., an enzyme, a process referred to as saccharification. The materials that include the cellulose are treated with the enzyme, e.g., by combining the material and the enzyme in a solvent, e.g., in an aqueous solution.

Figure 22:
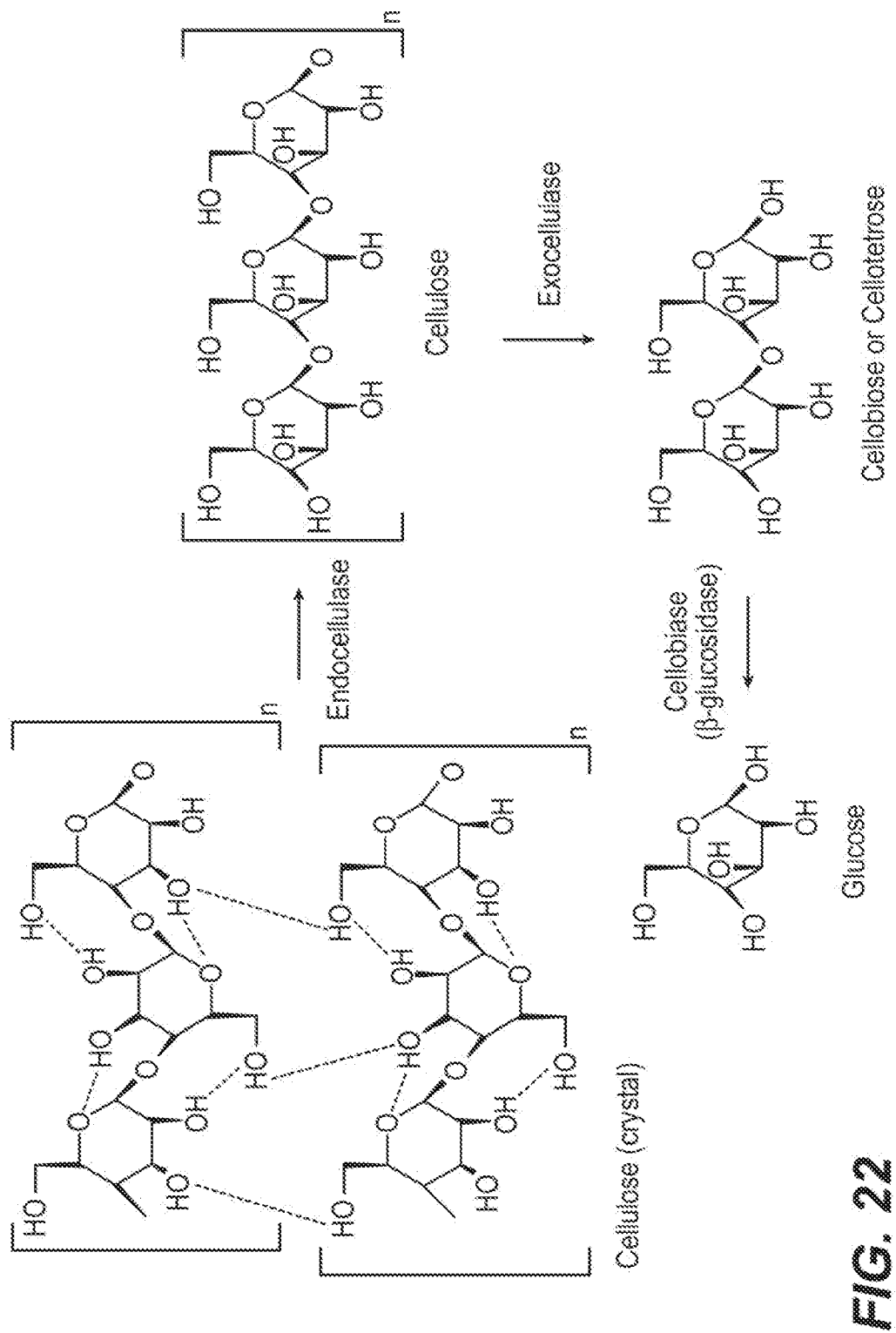
FIG. 22 is a diagram illustrating the enzymatic hydrolysis of cellulose to glucose.

Enzymes and organisms that break down cellulose contain or manufacture various cellulolytic enzymes (cellulases), ligninases or various small molecule biomass-destroying metabolites. These enzymes may be a complex of enzymes that act synergistically to degrade crystalline cellulose. Examples of cellulolytic enzymes include: endoglucanases, cellobiohydrolases, and cellobiases (β-glucosidases). Referring to FIG. 22, a cellulosic substrate is initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally cellobiase cleaves cellobiose to yield glucose.

Suitable saccharifying agents are described, for example, in the Materials section below.

As noted above, a food-based nutrient source or nutrient package is preferably added prior to or during saccharification, and an enzyme is added that is selected to release nutrients from the food-based nutrient source. Suitable enzymes are described, for example, in the Materials section below.

The saccharification process can be partially or completely performed in a tank (e.g., a tank having a volume of at least 4000, 40,000, 400,000 L or 1,000,000 L) in a manufacturing plant, and/or can be partially or completely performed in transit, e.g., in a rail car, tanker truck, or in a supertanker or the hold of a ship. The time required for complete saccharification will depend on the process conditions and the feedstock and enzyme used. If saccharification is performed in a manufacturing plant under controlled conditions, the cellulose may be substantially entirely converted to glucose in about 12-96 hours. If saccharification is performed partially or completely in transit, saccharification may take longer.

It is generally preferred that the tank contents be mixed during saccharification, e.g., using jet mixing as described in U.S. application Ser. No. 12/782,694, filed May 18, 2010, now U.S. Pat. No. 8,636,402; U.S. Ser. No. 13/293,977, filed Nov. 10, 2011, now U.S. Pat. No. 8,669,099; and U.S. Ser. No. 13/293,985, filed Nov. 10, 2011, the full disclosure of which are incorporated by reference herein.

The addition of surfactants can enhance the rate of saccharification. Examples of surfactants include non-ionic surfactants, such as a TWEEN® 20 or TWEEN® 80 polyethylene glycol surfactants, ionic surfactants, or amphoteric surfactants.

It is generally preferred that the concentration of the resulting glucose solution be relatively high, e.g., greater than 40%, or greater than 50, 60, 70, 80, 90 or even greater than 95% by weight. This reduces the volume to be shipped, if saccharification and fermentation are performed at different locations, and also inhibits microbial growth in the solution. However, lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin. Antibiotics will inhibit growth of microorganisms during transport and storage, and can be used at appropriate concentrations, e.g., between 15 and 1000 ppm by weight, e.g., between 25 and 500 ppm, or between 50 and 150 ppm. If desired, an antibiotic can be included even if the sugar concentration is relatively high.

A relatively high concentration solution can be obtained by limiting the amount of water added to the feedstock with the enzyme. The concentration can be controlled, e.g., by controlling how much saccharification takes place. For example, concentration can be increased by adding more feedstock to the solution. In order to keep the sugar that is being produced in solution, a surfactant can be added, e.g., one of those discussed above. Solubility can also be increased by increasing the temperature of the solution. For example, the solution can be maintained at a temperature of 40-50° C., 60-80° C., or even higher.

In some embodiments, the feedstock is processed to convert it to a convenient and concentrated solid material, e.g., in a powdered, granulate or particulate form. The concentrated material can be in a purified, or a raw or crude form. The concentrated form can have, for example, a total sugar concentration of between about 90 percent by weight and about 100 percent by weight, e.g., 92, 94, 96 or 98 percent by weight sugar. Such a form can be particularly cost effective to ship, e.g., to a bioprocessing facility, such as a biofuel manufacturing plant. Such a form can also be advantageous to store and handle, easier to manufacture and becomes both an intermediate and a product, providing an option to the biorefinery as to which products to manufacture.

In some instances, the powdered, granulate or particulate material can also include one or more of the materials, e.g., additives or chemicals, described herein, such as the food-based nutrient or nutrient package, a nitrogen source, e.g., urea, a surfactant, an enzyme, or any microorganism described herein. In some instances, all materials needed for a bio-process are combined in the powdered, granulate or particulate material. Such a form can be a particularly convenient form for transporting to a remote bioprocessing facility, such as a remote biofuels manufacturing facility. Such a form can also be advantageous to store and handle.

In some instances, the powdered, granulate or particulate material (with or without added materials, such as additives and chemicals) can be treated by any of the physical treatments described in U.S. Ser. No. 12/429,045, incorporated by reference above. For example, irradiating the powdered, granulate or particulate material can increase its solubility and can sterilize the material so that a bioprocessing facility can integrate the material into their process directly as may be required for a contemplated intermediate or product.

In certain instances, the powdered, granulate or particulate material (with or without added materials, such as additives and chemicals) can be carried in a structure or a carrier for ease of transport, storage or handling. For example, the structure or carrier can include or incorporate a bag or liner, such as a degradable bag or liner. Such a form can be particularly useful for adding directly to a bioprocess system.

Fermentation

Microorganisms can produce a number of useful intermediates and products by fermenting a low molecular weight sugar produced by saccharifying the paper feedstock materials. For example, fermentation or other bioprocesses can produce alcohols, organic acids, hydrocarbons, hydrogen, proteins or mixtures of any of these materials.

Yeast and *Zymomonas* bacteria, for example, can be used for fermentation or conversion. Other microorganisms are discussed in the Materials section, below. The optimum pH for fermentations is about pH 4 to 7. For example, the optimum pH for yeast is from about pH 4 to 5, while the optimum pH for *Zymomonas* is from about pH 5 to 6. Typical fermentation times are about 24 to 168 hours (e.g., 24 to 96 hrs) with temperatures in the range of 20° C. to 40° C. (e.g., 26° C. to 40° C.), however thermophilic microorganisms prefer higher temperatures.

In some embodiments e.g., when anaerobic organisms are used, at least a portion of the fermentation is conducted in the absence of oxygen e.g., under a blanket of an inert gas such as $N_2$, Ar, He, $CO_2$ or mixtures thereof. Additionally, the mixture may have a constant purge of an inert gas flowing through the tank during part of or all of the fermentation. In some cases, anaerobic condition can be achieved or maintained by carbon dioxide production during the fermentation and no additional inert gas is needed.

In some embodiments, all or a portion of the fermentation process can be interrupted before the low molecular weight sugar is completely converted to a product (e.g, ethanol). The intermediate fermentation products include high concentrations of sugar and carbohydrates. The sugars and carbohydrates can be isolated as discussed below. These intermediate fermentation products can be used in preparation of food for human or animal consumption. Additionally or alternatively, the intermediate fermentation products can be ground to a fine particle size in a stainless-steel laboratory mill to produce a flour-like substance.

The fermentations include the methods and products that are disclosed in U.S. Provisional Application Ser. No. 61/579,559, filed Dec. 22, 2012, and U.S. application 61/579,576, filed Dec. 22, 2012 incorporated by reference herein in its entirety.

Mobile fermentors can be utilized, as described in U.S. Provisional Patent Application Ser. 60/832,735, now Published International Application No. WO 2008/011598. Similarly, the saccharification equipment can be mobile. Further, saccharification and/or fermentation may be performed in part or entirely during transit.

Distillation

After fermentation, the resulting fluids can be distilled using, for example, a "beer column" to separate ethanol and other alcohols from the majority of water and residual solids. The vapor exiting the beer column can be, e.g., 35% by weight ethanol and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Other Possible Processing of Sugars

Processing during or after saccharification can include isolation and/or concentration of sugars by chromatography e.g., simulated moving bed chromatography, precipitation, centrifugation, crystallization, solvent evaporation and combinations thereof. In addition, or optionally, processing can include isomerization of one or more of the sugars in the sugar solution or suspension. Additionally, or optionally, the sugar solution or suspension can be chemically processed e.g., glucose and xylose can be hydrogenated to sorbitol and xylitol respectively. Hydrogenation can be accomplished by use of a catalyst e.g., Pt/$\gamma$-$Al_2O_3$, Ru/C, Raney Nickel in combination with $H_2$ under high pressure e.g., 10 to 12000 psi.

Some possible processing steps are disclosed in U.S. Provisional Application Ser. No. 61/579,552, filed Dec. 22, 2012, and in U.S. Provisional Application Ser. No. 61/579,576 filed Dec. 22, 2012, incorporated by reference herein in its entirety above.

Removing of Fillers, Inks, and Coatings

Paper feedstock used in the processes described can contain fillers, coatings, laminated material, pigments, inks and binders. These can be removed and either discarded or recycled as described here.

Inorganic fillers and coatings e.g., those described in the materials section below can be removed at any point during the process. For example, the inorganic filler and coating can be removed from the feedstock after a mechanical, physical or chemical treatment to reduce the recalcitrance of the feedstock; after combination with a fluid; after, during or before saccharification; after, during or before a purification step; after, during or before a fermentation step; and/or after, during or before a chemical conversion step. The fillers and coatings can be removed by any means e.g., by sedimentation, precipitation, ligand sequestration, filtration, floatation, chemical conversion and centrifugation. Some of the physical treatments discussed herein (see Physical Treatment section) can aid in separating the cellulosic materials from the inorganic fillers and coatings (e.g., mechanical treatments, chemical treatments, irradiation, pyrolysis, sonication and/or oxidation). The recovered inorganic fillers can be recycled or discarded.

Inks that are present can be removed from the feedstock at any point during the process. Inks can be a complex medium composed of several components e.g., solvents, pigments, dyes, resins, lubricants, solubilizers, surfactants, particulate matter and/or fluorescers. For example, printed papers, e.g., magazines and catalogs, may include high levels of the pigments generally used in printing inks. In some cases the papers include metal-based pigments, organic pigments, and/or Lake pigments. For example, pigments that can be used are Yellow Lakes, Tartrazine Yellow Lake, Hansa Yellows, Diarylide Yellows, Yellow azo pigments, Fluorescent Yellow, Diarylide Orange, DNA Orange, Pyrazolone Orange, Fast Orange F2G, Benzimidazolone Orange HL, Ethyl Lake Red C, Para Reds, Toluidine Red, Carmine F.B., Naphthol Reds and Rubines, Permanent Red FRC, Bordeaux FRR, Rubine Reds, Lithol Reds, BON Red, Lithol Rubine 4B, BON Maroon, Rhodamine 6G, Lake Red C, BON Arylamide Red, Quinacrinone Magentas, Copper Ferrocyanide Pink, Benzimidazolone Carmines and Reds, Azo Magenta G, Anthraquinone Scarlet, Madder Lakes, Phthalocyanine Blues, PMTA Victoria Blue, Victoria Blue CFA, Ultramarine Blue, Indanthrene Blue, Alkali Blues, Peacock Blue, Benzimidazolone Bordeaux HF 3R, PMTA Rhodamine, PMTA Violet, Dioxazine Violet, Carbazole Violet, Crystal Violet, Dioxazine Violet B, Thioindigoid Red, Phthalocyanine Greens, PMTA Greens, Benzimidazolone Brown HFR, Cadmium Red, Cadmium Yellow, Cadmium Oranges, Cadmium-Mercury Reds, Iron Oxide Yellows, Irons Oxide Blues, Iron Oxide browns, Iron Oxide Reds, Ultramarine Blues, Ultramarine Violet, Chromium Antimony Titanium Buff, copper phthalocyanine blue, green copper phthalocyanine pigments, potash blue and soda blue pigments. The removal of ink may help improve certain parts in the process. For example, some ink can be toxic to microorganisms used in the process. The inks can also impart an undesirable coloration or toxicity to the final product. Furthermore, removing the inks may allow these to be recycled, improving the cost benefits to the process and lessening the environmental impact of the paper feedstock. The inks can be removed by any means. For example, removal may include dispersion, floatation, pressing and/or washing steps, extraction with solvents (e.g., supercritical $CO_2$, alcohol, water and organic solvents), settling, chemical means, sieving and/or precipitation. Some of the physical treatments discussed herein (see Physical Treatment section) can aid in separating the cellulosic materials from the inks (e.g., mechanical treatments, chemical treatments, irradiation, pyrolysis, sonication and/or oxidation). In addition enzymatic deinking technologies such as those disclosed in U.S. Pat. No. 7,297,224 hereby incorporated by reference herein, can be used.

Coating materials, e.g., those found in poly-coated paper described in the materials section below, can be removed from the feedstock at any point during the process. This can be done by, for example, the methods mentioned above for removal of pigments and inks and inorganic materials. In some cases, where polycoated paper is a laminate, delamination can be done by, for example, chemical and/or mechanical means. The non-cellulosic laminate portions can then be separated from the cellulose containing layers and discarded and/or recycled.

Intermediates and Products

The processes and nutrients discussed herein can be used to convert paper feedstocks to one or more products, such as energy, fuels, foods and materials. Specific examples of products include, but are not limited to, hydrogen, sugars (e.g., glucose, xylose, arabinose, mannose, galactose, fructose, disaccharides, oligosaccharides and polysaccharides), alcohols (e.g., monohydric alcohols or dihydric alcohols, such as ethanol, n-propanol, isobutanol, sec-butanol, tert-butanol or n-butanol), hydrated or hydrous alcohols, e.g., containing greater than 10%, 20%, 30% or even greater than 40% water, sugars, biodiesel, organic acids (e.g., acetic acid and/or lactic acid), hydrocarbons, e.g., methane, ethane, propane, isobutene, pentane, n-hexane, biodiesel, bio-gasoline and mixtures thereof, co-products (e.g., proteins, such as cellulolytic proteins (enzymes) or single cell proteins), and mixtures of any of these in any combination or relative concentration, and optionally in combination with any additives, e.g., fuel additives. Other examples include carboxylic acids, such as acetic acid or butyric acid, salts of a carboxylic acid, a mixture of carboxylic acids and salts of carboxylic acids and esters of carboxylic acids (e.g., methyl, ethyl and n-propyl esters), ketones, aldehydes, alpha, beta unsaturated acids, such as acrylic acid and olefins, such as ethylene. Other alcohols and alcohol derivatives include propanol, propylene glycol, 1,4-butanediol, 1,3-propanediol, sugar alcohols (e.g., erythritol, glycol, glycerol, sorbitol threitol, arabitol, ribitol, mannitol, dulcitol, fucitol, iditol, isomalt, maltitol, lactitol, xylitol and other polyols), methyl or ethyl esters of any of these alcohols. Other products include methyl acrylate and methylmethacrylate. The product may also be an organic acid, e.g., lactic acid, formic acid, acetic acid, propionic acid, butyric acid, succinic acid, valeric acid, caproic, palmitic acid, stearic acid, oxalic acid, malonic acid, glutaric acid, oleic acid, linoleic acid, glycolic acid, γ-hydroxybutyric acid, a mixture thereof, a salt of any of these acids, or a mixture of any of the acids and their respective salts.

Other intermediates and products, including food and pharmaceutical products, are described in U.S. Ser. No. 12/417,900, the full disclosure of which is hereby incorporated by reference herein.

Materials

Paper Feedstocks

Suitable paper feedstocks include paper that is highly pigmented, coated or filled and can have a low calorific value. Sources of such paper include magazines, catalogs, books, manuals, labels, calendars, greeting cards and other high quality printed materials such as prospectuses, brochures and the like. The papers may include at least 0.025% by weight of pigment, filler or coating, e.g., from 0 to 80%, 0 to 50%, 0.1 to 50%, 0.1 to 30%, 0.1 to 20%, 0.5 to 2.5%, 0.2 to 15%, 0.3 to 10%, 0.5 to 5%.

Other suitable paper feedstocks include high basis weight coated paper and/or paper with a high filler content i.e., at least 10 wt. %. These papers can be printed or unprinted. Examples of this type of feedstock include paper having a basis weight, as defined as the weight in pounds (lb) for a ream (500 sheets) of 25"×38" sheets, of at least 35 lb., for example at least 45 lb., at least 50 lb., at least 60 lb, at least 70 lb. or at least 80 lb. The feedstock includes paper having a basis weight below 330 lb., for example below about 300 lb, below about 250 lb, below about 200 lb, below about 150 lb, below about 120 lb, below about 110 lb, below about 105 lb or below about 100 lb. For example the basis weight may be between 35 lb and 330 lb, 35 lb and 120 lb, between 35 lb and 110 lb, between 35 lb and 100 lb, between 35 lb and 90 lb, between 45 lb and 120 lb, between 45 lb and 110 lb, between 45 lb and 100 lb, between 45 lb and 90 lb, between 50 lb and 120 lb, between 50 lb and 110 lb, between 50 lb and 100 lb, between 50 lb and 90 lb, between 60 lb and 120 lb, between 60 lb and 110 lb, between 60 lb and 100 lb, between 60 lb and 90 lb, between 60 lb and 120 lb, between 60 lb and 110 lb, between 60 lb and 100 lb, between 60 lb and 90 lb, between 70 lb and 120 lb, between 70 lb and 110 lb, between 70 lb and 100 lb, between 70 lb and 90 lb, between 90 lb and 330 lb, between 90 lb and 300 lb, between 90 lb and 250 lb, between 90 lb and 200 lb, between 90 lb and 150 lb, between 90 lb and 110 lb, between 110 lb and 330 lb, between 110 lb and 300 lb, between 110 lb and 250 lb, between 110 lb and 200 lb, between 110 lb and 150 lb, between 130 lb and 330 lb, between 130 lb and 300 lb, between 130 lb and 250 lb, between 130 lb and 200 lb, or between 130 lb and 150 lb, In some embodiments, the papers have relatively high density, e.g., greater than 1.11 $g/cm^3$, in some cases from about 1.11 to 2 $g/cm^3$ e.g., 1.11 to 1.8 $g/cm^3$, 1.11 to 1.6 $g/cm^3$, 1.11 to 1.52 $g/cm^3$, 1.2 to 1.8 $g/cm^3$, 1.2 to 1.6 $g/cm^3$, 1.2 to 1.52 $g/cm^3$, 1.3 to 1.8 $g/cm^3$, 1.3 to 1.6 $g/cm^3$ or 1.3 to 1.52 $g/cm^3$. Such papers often have a high ash content e.g., at least 8 wt. %, at least 10 wt. %, at least 15 wt. %, at least 20 wt. % or at least 50 wt. %. The ash content can be between 8 and 50%, e.g., between 10 and 50%, between 20 and 50%, between 30 and 50%, between 10 and 40%, between 20 and 40%, between 10 and 30% or between 10 and 20%. The papers can have a high filler content, e.g., at least 10% by weight, e.g., at least 20 wt %, at least 30 wt %, at least 40 wt % or at least 50 wt %. Filler contents can be between 10 and 80%, e.g., between 20 and 80%, between 30 and 80%, between 40 and 80%, between 10 and 70%, between 20 and 70%, between 30 and 70%, between 40 and 70%, between 10 and 60%, between 20 and 60%, between 30 and 60% and between 40 and 60%. Suitable fillers include clays, oxides (e.g., titania, silica, alumina), carbonates (e.g., calcium carbonate), silicates (e.g., Talc) and aluminosilicates (e.g., Kaolin). One suitable grade of coated paper is referred to in the industry as Machine Finished Coated (MFC) paper. In other embodiments the paper can have a high surface density (i.e., Grammage), for example, at least 50 $g/m^2$, at least 60 $g/m^2$, at least 70 $g/m^2$, at least 80 $g/m^2$ or at least 90 $g/m^2$. The Grammage can be between 50 $g/m^2$ and 200 $g/m^2$, between 50 $g/m^2$ and 175 $g/m^2$, between 50 $g/m^2$ and 150 $g/m^2$, between 50 $g/m^2$ and 125 $g/m^2$, between 50 $g/m^2$ and 100 $g/m^2$, between 60 $g/m^2$ and 200 $g/m^2$, between 60 $g/m^2$ and 175 $g/m^2$, between 60 $g/m^2$ and 150 $g/m^2$, between 60 $g/m^2$ and 125 $g/m^2$, between 60 $g/m^2$ and 100 $g/m^2$, between 70 $g/m^2$ and 200 $g/m^2$, between 70 $g/m^2$ and 175 $g/m^2$, between 70 $g/m^2$ and 150 $g/m^2$, between 70 $g/m^2$ and 125 $g/m^2$, between 70 $g/m^2$ and 100 $g/m^2$, between 80 $g/m^2$ and 200 $g/m^2$, between 80 $g/m^2$ and 175 $g/m^2$, between 80 $g/m^2$ and 150 $g/m^2$, between 80 $g/m^2$ and 125 $g/m^2$, between 80 $g/m^2$ and 100 $g/m^2$, between 130 $g/m^2$ and 500 $g/m^2$, between 130 $g/m^2$ and 450 $g/m^2$, between 130 $g/m^2$ and 350 $g/m^2$, between 130 $g/m^2$ and 300 $g/m^2$, between 130 $g/m^2$ and 250 $g/m^2$, between 130 $g/m^2$ and 200 $g/m^2$, between 130 $g/m^2$ and 175 $g/m^2$, between 130 $g/m^2$ and 150 $g/m^2$, between 200 $g/m^2$ and 500 $g/m^2$, between 200 $g/m^2$ and 450 $g/m^2$, between 200 $g/m^2$ and 350 $g/m^2$, between 200 $g/m^2$ and 300 $g/m^2$, between 200 $g/m^2$ and 250 $g/m^2$, between 250 $g/m^2$ and 500 $g/m^2$, between 250 $g/m^2$ and 450 $g/m^2$, between 250 $g/m^2$ and 350 $g/m^2$, between 250 $g/m^2$ and 300 $g/m^2$, between 200 $g/m^2$ and 250 $g/m^2$, between 300 $g/m^2$ and 500 $g/m^2$, between 300 $g/m^2$ and 450 $g/m^2$, or between 300 $g/m^2$ and 350 $g/m^2$.

Coated papers are well known in the paper art, and are disclosed, for example, in U.S. Pat. Nos. 6,777,075; 6,783,804, and 7,625,441, the full disclosures of which are incorporated herein by reference.

Coated papers suitable as feedstock can include paper coated with an inorganic material, for example the same materials used as fillers can be used in coatings. Additionally, coated papers can include paper coated with a polymer (poly-coated paper). Such paper can be made, for example, by extrusion coating, brush coating, curtain coating, blade coating, air knife coating, cast coating or roller coating paper. For example, sources of such poly-coated paper include a variety of food containers, including juice cartons, condiment pouches (e.g., sugar, salt, pepper), plates, pet food bags, cups, bowls, trays and boxes for frozen foods. The poly-coated paper can, in addition to paper, contain, for example, polymers, (e.g., polyethylene, polypropylene, biodegradable polymers, silicone), latexes, binders, wax, and, in some cases, one or more layers of aluminum. The poly coated papers can be multi layered laminate, for example, made with one or more, e.g., two, three, four, five or more, layers of polyethylene and paper and one or more, e.g., two, three or more layers of aluminum.

The paper feedstocks typically have a low gross caloric value e.g., below 7500 Btu/lb e.g, below 7400 Btu/lb, below 7200 Btu/lb, below 7000 Btu/lb, below 6800 Btu/lb, below 6600 Btu/lb, below 6400 Btu/lb, below 6200 Btu/lb, below 6000 Btu/lb, below 5800 Btu/lb, below 5600 Btu/lb, below 5400 Btu/lb or below 5200 Btu/lb. The gross calorific value can be between about 5200 and 7500 Btu/lb e.g., between 6800 and 7000 Btu/lb, between 6700 and 7100 Btu/lb, between 6400 and 7100 Btu/lb, between 6600 and 6800 Btu/lb, between 6100 and 6700 Btu/lb, between 6100 and 6300 Btu/lb, between 6000 and 6350 Btu/lb, between 5600 and 6400 Btu/lb or between 5200 and 5500 Btu/lb. The gross calorific value can be measure using a bomb calorimeter e.g., as outlined in ASTM method E711.

The paper feedstock can have a basis weight between 35 lb and 330 lb, e.g. 45 lb and 330 lb, 60 and 330 lb, 80 and 330 lb, 60 and 200 lb, 60 and 100 lb; optionally a filler content greater than about 10 wt. %, e.g., between 10 and 80 wt. %, between 20 and 80 wt. %, between 30 and 80 wt. %, between 30 and 70 wt. %, between 230 and 60 wt. %; optionally a grammage between 50 and 500 $g/m^2$, e.g., 70 and 500 $g/m^2$, 90 and 500 $g/m^2$, 90 and 400 $g/m^2$, 90 and 300 $g/m^2$, 90 and 200 $g/m^2$; and optionally a calorific value between 7500 and 4000 Btu/lb, e.g., 7000 and 4000 Btu/lb, 6500 and 4000 Btu/lb, 5000 and 4000 Btu/lb, 6000 and 4500

Btu/lb; optionally an ash content between 8 and 50 wt. %, e.g., 10 and 80 wt. %, 10 and 60 wt. %, 10 and 50 wt. %, 20 and 50 wt. %.

Some suitable paper feedstock can include a homogeneous sheet formed by irregularly intertwining cellulose fibers. These can include, for example, Abrasive Papers, Absorbent Paper, Acid Free Paper, Acid Proof Paper, Account Book Paper, Adhesive Paper, Air Dried Paper, Air Filter Paper, Album Paper, Albumin Paper, Alkaline Paper, Alligator Imitation Paper, Aluminum Foil Laminated paper, Ammunition Paper, Announcement Card Paper, Anti Rust Paper, Anti-Tarnish Paper, Antique Paper, Archival Paper, Art Paper, Asphalt Laminated Paper, Azurelaid Paper, Back Liner Paper, Bacon Paper, Bagasse Paper, Bakers' Wrap, Balloon Paper, Banknote or Currency Paper, Barograph Paper, Barrier Paper, Baryta Paper, Beedi Wrap Paper, Bible Paper, Black Waterproof Paper, Blade Wrapping Paper, Bloodproof Paper or Butcher Paper, Blotting Paper, Blueprint Paper, Board, Bogus Paper, Bond Paper, Book Paper, Boxboard, Braille Printing Paper, Bread Wrapping Paper, Bristol Board, Business Form Paper, Butter Wrapping Paper, Burnt Paper, Cable Paper, Calf Paper, Calico Paper, Candy Twisting Tissue, Canvas Paper, Carbonless Paper, Cardboard, Corrugated Cardboard, Carton board, Cartridge paper, Cast Coated Paper, Catalogue Paper, Chart Paper, Check Paper, Cheese Wrapping Paper, Chipboard, Chromo, Coarse Paper (also Industrial Paper), Coated freesheet, Coated Paper, Coated White Top Liner, Cockle Finish Paper, Color-fast papers, Commodity Paper, Colored Kraft, Condenser Tissue, Construction Paper, Containerboard, Copier Paper or Laser Paper, Correspondence Papers, Corrugated Board, Corrugated Medium or Fluting Media or Media, Cotton Paper or Rag Paper, Cover Paper or Cover Stock, Creamwove Paper, Cut Sheet, Damask Paper, Decalcomania Paper, Diazo Base Paper, Document Paper, Drawing Paper, Duplex Board, Duplex Paper, End-leaf Paper, Envelop Paper, Esparto Paper, Extensible Kraft, Extrusion Coated Board, Fax Base Paper, Flame Resistant, Flocked Paper, Fluorescent Paper, Folding Boxboard, Form Bond, Freesheet, Fruit Wrapping Paper, Gasket Board, Glassine Paper, Glazed Paper, Granite Paper, Gravure Paper, Gray Board, Greaseproof Paper, Green Paper, Groundwood Papers, Gummed Paper, Gypsum Board, Handmade Paper, Hanging Paper, Hard Sized Paper, Heat Seal Paper, Heat Transfer Paper, Hi-Fi (High Finish) Paper, Industrial Papers, Insect Resistant, Insulating Board, Ivory Board, Japan Paper, Jute Paper, Kraft Bag Paper, Kraft liner, Kraft Paper, Kraft Waterproof Paper, Kraft Wrapping Paper, Label Paper, Lace Paper, Laid Paper, Laminated Paper, Laminated Linerboard, Latex Paper, Ledger Paper, Lightproof Paper, Liner, Linerboard, Litmus Paper, On Machine Coated, Magazine Paper, Manila, Map Paper, Marble Paper, Matrix Paper, Matt Finished Paper, Mechanical Paper, Mellow Paper, Metalization Base Paper, Machine Finished Paper, Machine glazed Paper, Millboard, Mulberry Paper, Natural Colored Papers or Self Colored Papers, Newsprint, Oatmeal Paper, Offset Paper, Packaging Paper, Paperboard, Pattern Paper, Permanent Paper, Photographic Paper, Playing Card Stock, Pleading Paper, Poly Extrusion Paper, Postcard Board, Post-Consumer Waste Paper, Poster Paper, Pre-Consumer Waste Paper, Pressure Sensitive Coated Paper, Publishing Paper, Pulp Board, Release Paper, Roofing Paper, Safety Paper, Security paper, Self Adhesive Paper, Self Contained Paper, Silicon Treated Paper, Single Faced Corrugated Board, Sized Paper, Stamp Paper, Strawboard, Suede Paper, Supercalendered Paper, Surface-Sized, Super Art Paper, Synthetic Fiber Paper, Tag Paper, Testliner, Text Paper, Thermal Paper, Translucent Drawing Paper, Transparent Paper, Treated Paper, Union Kraft, Unglazed Paper, Un-sized Paper, Vaporproof Paper, Varnish-Label Paper, Vegetable Parchment, Vellum Paper, Velour Paper, Velvet Finish Paper, Vulcanizing Paper, Wadding, Wall Paper, Water-Color Paper, Water Finished Paper, Water Resistant Paper, Waterleaf, Waxed Paper, Wet Strength Paper, White Top Liner, Willesden Paper, Wipes or Wiper, Wove, Wrapper, Writing Paper and Xerographic Paper.

The feedstocks described herein can be used in combination with any of the biomass feedstocks described in U.S. application Ser. No. 12/417,880, filed Apr. 3, 2009, incorporated by reference herein in its entirety.

Saccharifying Agents

Suitable enzymes include cellobiases and cellulases capable of degrading biomass.

Suitable cellobiases include a cellobiase from *Aspergillus niger* sold under the tradename NOVOZYME 188™ enzymes.

Cellulases are capable of degrading biomass, and may be of fungal or bacterial origin. Suitable enzymes include cellulases from the genera *Bacillus, Pseudomonas, Humicola, Fusarium, Thielavia, Acremonium, Chrysosporium* and *Trichoderma*, and include species of *Humicola, Coprinus, Thielavia, Fusarium, Myceliophthora, Acremonium, Cephalosporium, Scytalidium, Penicillium* or *Aspergillus* (see, e.g., EP 458162), especially those produced by a strain selected from the species *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum,* and *Acremonium furatum*; preferably from the species *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additionally, *Trichoderma* (particularly *Trichoderma viride, Trichoderma reesei,* and *Trichoderma koningii*), alkalophilic *Bacillus* (see, for example, U.S. Pat. No. 3,844,890 and EP 458162), and *Streptomyces* (see, e.g., EP 458162) may be used.

Enzyme complexes may be utilized, such as those available from GENENCOR® under the tradename ACCELLERASE®, for example, ACCELLERASE® 1500 enzyme complex. ACCELLERASE® 1500 enzyme complex contains multiple enzyme activities, mainly exoglucanase, endoglucanase (2200-2800 CMC U/g), hemi-cellulase, and beta-glucosidase (525-775 pNPG U/g), and has a pH of 4.6 to 5.0. The endoglucanase activity of the enzyme complex is expressed in carboxymethylcellulose activity units (CMC U), while the beta-glucosidase activity is reported in pNP-glucoside activity units (pNPG U). In one embodiment, a blend of ACCELLERASE® 1500 enzyme complex and NOVOZYME™ 188 cellobiase is used.

Fermentation Agents

The microorganism(s) used in fermentation can be natural microorganisms and/or engineered microorganisms. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures of organisms can be utilized.

Suitable fermenting microorganisms have the ability to convert carbohydrates, such as glucose, fructose, xylose, arabinose, mannose, galactose, oligosaccharides or polysaccharides into fermentation products. Fermenting microorganisms include strains of the genus *Saccharomyces* spp. e.g., *Saccharomyces cerevisiae* (baker's yeast), *Saccharomyces distaticus*, *Saccharomyces uvarum*; the genus *Kluyveromyces*, e.g., species *Kluyveromyces marxianus*, *Kluyveromyces fragilis*; the genus *Candida*, e.g., *Candida pseudotropicalis*, and *Candida brassicae, Pichia stipitis* (a relative of *Candida shehatae*, the genus *Clavispora*, e.g., species *Clavispora lusitaniae* and *Clavispora opuntiae*, the genus *Pachysolen*, e.g., species *Pachysolen tannophilus*, the genus *Bretannomyces*, e.g., species *Bretannomyces clausenii* (Philippidis, G. P., 1996, Cellulose bioconversion technology, in Handbook on Bioethanol: Production and Utilization, Wyman, C. E., ed., Taylor & Francis, Washington, D.C., 179-212). Other suitable microorganisms include, for example, *Zymomonas mobilis, Clostridium thermocellum* (Philippidis, 1996, supra), *Clostridium saccharobutylacetonicum, Clostridium saccharobutylicum, Clostridium Puniceum, Clostridium beijernckii, Clostridium acetobutylicum, Moniliella pollinis, Yarrowia lipolytica, Aureobasidium* sp., *Trichosporonoides* sp., *Trigonopsis variabilis, Trichosporon* sp., *Moniliellaacetoabutans, Typhula variabilis, Candida magnoliae, Ustilaginomycetes, Pseudozyma tsukubaensis*, yeast species of genera *Zygosaccharomyces, Debaryomyces, Hansenula* and *Pichia*, and fungi of the dematioid genus *Torula*.

Commercially available yeasts include, for example, RED STAR®/Lesaffre Ethanol Red yeast (available from Red Star/Lesaffre, USA), FALI® (available from Fleischmann's Yeast, a division of Burns Philip Food Inc., USA), SUPER-START® yeast (available from Alltech, now Lalemand), GERT STRAND® yeast (available from Gert Strand AB, Sweden) and FERMOL® yeast (available from DSM Specialties).

Nutrient Package Ingredients

As discussed above, it may be preferred to include a nutrient package in the system during saccharification and/or fermentation. Preferred nutrient packages contain a food-based nutrient source, a nitrogen source, and in some cases other ingredients, e.g., phosphates. Suitable food-based nutrient sources include grains and vegetables, including those discussed above and many others. The food-based nutrient source may include mixtures of two or more grains and/or vegetables. Such nutrient sources and packages are disclosed in U.S. application Ser. No. 13/184,138, incorporated by reference herein in its entirety above.

Enzymes for Releasing Nutrients

When a food-based nutrient source is utilized, it is preferred that the saccharification and/or fermentation mixture further include an enzyme system selected to release nutrients, e.g., nitrogen, amino acids, and fats, from the food-based nutrient source. For example, the enzyme system may include one or more enzymes selected from the group consisting of amylases, proteases, and mixtures thereof. Such systems are disclosed in U.S. application Ser. No. 13/184,138, incorporated by reference herein in its entirety.

Fuel Cells

Where the methods described herein produce a sugar solution or suspension, this solution or suspension can subsequently be used in a fuel cell. For example, fuel cells utilizing sugars derived from cellulosic or lignocellulosic materials are disclosed in U.S. Provisional Application Ser. No. 61/579,568, filed Dec. 22, 2011, the complete disclosure of which is incorporated herein by reference.

Other Embodiments

A number of embodiments of the invention have been described. Nevertheless, it will be understood that various modifications may be made without departing from the spirit and scope of the invention. For example, the jet mixers described herein can be used in any desired combination, and/or in combination with other types of mixers.

The jet mixer(s) may be mounted in any desired position within the tank. With regard to shaft-mounted jet mixers, the shaft may be collinear with the center axis of the tank or may be offset therefrom. For example, if desired the tank may be provided with a centrally mounted mixer of a different type, e.g., a marine impeller or Rushton impeller, and a jet mixer may be mounted in another area of the tank either offset from the center axis or on the center axis. In the latter case one mixer can extend from the top of the tank while the other extends upward from the floor of the tank.

In any of the jet mixing systems described herein, the flow of fluid (liquid and/or gas) through the jet mixer can be continuous or pulsed, or a combination of periods of continuous flow with intervals of pulsed flow. When the flow is pulsed, pulsing can be regular or irregular. In the latter case, the motor that drives the fluid flow can be programmed, for example to provide pulsed flow at intervals to prevent mixing from becoming "stuck." The frequency of pulsed flow can be, for example, from about 0.5 Hz to about 10 Hz, e.g., about 0.5 Hz, 0.75 Hz, 1.0 Hz, 2.0 Hz, 5 Hz, or 10 Hz. Pulsed flow can be provided by turning the motor on and off, and/or by providing a flow diverter that interrupts flow of the fluid.

While tanks have been referred to herein, jet mixing may be used in any type of vessel or container, including lagoons, pools, ponds and the like. If the container in which mixing takes place is an in-ground structure such as a lagoon, it may be lined. The container may be covered, e.g., if it is outdoors, or uncovered.

For example, while it is possible to perform all the processes described herein at one physical location, in some embodiments, the processes are completed at multiple sites, and/or may be performed during transport.

Accordingly, other embodiments are within the scope of the following claims.

What is claimed is:

1. A method of saccharifying paper feedstock, the method comprising:
    providing in a vessel, a slurry comprising a paper feedstock consisting essentially of polycoated paper, water, and an enzyme, the slurry having greater than 20 weight percent solids of the paper feedstock;
    drawing slurry material from the vessel and jetting the slurry material into the vessel, while saccharifying at least a portion of the paper feedstock, producing a sugar; and
    after saccharification, removing from the slurry material a polymer residue from the polycoated paper.

2. The method of claim 1, wherein jetting the slurry material comprises providing a jet mixer having a nozzle, and directing the slurry material through the nozzle under pressure.

3. The method of claim 2, wherein a pump generates the pressure, the nozzle being in fluid communication with the pump.

4. The method of claim 2, wherein the nozzle comprises a shroud surrounding an impeller, the impeller configured to provide jet flow through the nozzle.

5. The method of claim 1, wherein jetting the slurry material comprises directing the slurry material through a plurality of nozzles under pressure, the pressure generated by one or more pumps, each of the plurality of nozzles being in fluid communication with at least one of the one or more pumps.

6. The method of claim 1, wherein jetting the slurry material comprises drawing slurry material through an inlet to a pump, the inlet being in fluid communication with the vessel; and
   pumping the slurry material through a nozzle under pressure, the nozzle being in fluid communication with the pump.

7. The method of claim 6, wherein the pump is located outside of the vessel.

8. The method of claim 6, wherein the inlet draws slurry material from near the surface of the slurry in the vessel.

9. The method of claim 6, wherein the inlet draws slurry material from near the bottom surface of the vessel.

10. The method of claim 1, wherein the slurry material jets into the vessel through a nozzle at a velocity between 5 to 150 meters per second.

11. The method of claim 1, wherein jetting the slurry material into the vessel, causes a secondary entrained flow of aqueous slurry material in the vessel.

12. The method of claim 1, wherein jetting the slurry material into the vessel provides effective mixing in the vessel while minimizing damage to the enzyme.

13. The method of claim 1, wherein the vessel has a flat bottom surface.

14. The method of claim 1, wherein the vessel has an arcuate bottom surface.

15. The method of claim 1, wherein the vessel has a volume of at least 4,000 L.

16. The method of claim 1, wherein the vessel has a volume of at least 40,000 L.

17. The method of claim 1, wherein the initial solids concentration of the paper feedstock in the slurry is at least 20 weight percent.

18. The method of claim 1, wherein the paper feedstock comprises paper having a pigment, filler, and/or coating content of at least 20 weight percent.

19. The method of claim 1, wherein the paper feedstock comprises paper having an ash content of at least 8 weight percent.

20. The method of claim 1, wherein the paper feedstock has been exposed to irradiation, the irradiation provided by one or more of: an ion beam and an electron beam.

21. The method of claim 20, wherein the paper feedstock has received at least at least 10 Mrad of irradiation.

22. The method of claim 20, wherein the paper feedstock has received irradiation at a dose rate of at least 1 Mrad per second.

23. The method of claim 1, wherein the paper feedstock has been subjected to a physical treatment, the physical treatment effective to reduce the bulk density of the paper feedstock and/or increase the BET surface area of the paper feedstock.

24. The method of claim 1, wherein the paper feedstock has a bulk density of less than about 0.5 grams per cubic centimeter.

25. The method of claim 1, wherein the enzyme comprises a cellulase.

26. The method of claim 1, further comprising fermenting at least a portion of the sugar with a microorganism.

27. The method of claim 26, wherein the paper feedstock comprises a toxic material and/or a solid inorganic material.

28. The method of claim 27, wherein the toxic material comprises a pigment and/or an ink.

29. The method of claim 27, wherein the solid inorganic material comprises a filler, a coating, and/or a pigment.

* * * * *